US005794286A

United States Patent [19]

Scott et al.

[11] Patent Number: 5,794,286

[45] Date of Patent: Aug. 18, 1998

[54] PATIENT TREATMENT APPARATUS

[75] Inventors: Gerald R. Scott, Villa Park; James P. Moulton, Elgin, both of Ill.; V. Craig Seyl, Lenexa, Kans.; John L. Emrich, Algonquin; Wayne L. Peterson, St. Charles, both of Ill.

[73] Assignee: Standex International, Salem, N.H.

[21] Appl. No.: 527,555

[22] Filed: Sep. 13, 1995

[51] Int. Cl.[6] .......... A61F 5/01

[52] U.S. Cl. .......... 5/611; 5/612; 5/613; 128/845; 606/240

[58] Field of Search .......... 5/610, 611, 612, 5/613, 616, 621, 622, 623, 624; 606/240, 242; 128/845

[56] References Cited

U.S. PATENT DOCUMENTS

| | | | |
|---|---|---|---|
| 2,571,829 | 10/1951 | Buckley | 5/613 X |
| 2,926,660 | 3/1960 | Thompson | 5/613 X |
| 3,226,106 | 12/1965 | Johnson et al. | 5/613 |
| 3,579,066 | 5/1971 | Bearfield et al. . | |
| 3,640,520 | 2/1972 | Wieland et al. . | |
| 3,806,109 | 4/1974 | Weber et al. . | |
| 3,998,218 | 12/1976 | Lane et al. | 5/613 |
| 4,021,028 | 5/1977 | Weber et al. . | |
| 4,271,830 | 6/1981 | Moon | 5/610 |
| 4,401,110 | 8/1983 | Ekholm . | |
| 4,520,800 | 6/1985 | Kowalski . | |
| 4,523,581 | 6/1985 | Ekholm . | |
| 4,648,389 | 3/1987 | Kowalski et al. . | |
| 4,660,549 | 4/1987 | Kowalski et al. . | |
| 4,660,817 | 4/1987 | Kowalski . | |
| 4,722,328 | 2/1988 | Scott et al. . | |
| 4,724,554 | 2/1988 | Kowalski et al. . | |
| 4,850,343 | 7/1989 | Scott . | |
| 5,014,688 | 5/1991 | Fast . | |
| 5,054,142 | 10/1991 | Owens . | |
| 5,192,306 | 3/1993 | Scott et al. . | |
| 5,308,359 | 5/1994 | Lossing . | |
| 5,362,302 | 11/1994 | Jensen et al. | 5/612 X |

*Primary Examiner*—Michael F. Trettel

*Attorney, Agent, or Firm*—Mason, Kolehmainen, Rathburn and Wyss

[57] ABSTRACT

Treatment apparatus supporting a patient lying in a generally prone or supine position for manipulation includes a base and a table supported thereabove for movement between selected different horizontal positions or working levels for treatment of the patient. The table is tiltable toward and away from an upright position for facilitating the patient in mounting and dismounting before and after treatment and includes a foot piece adjacent an end of the table for supporting the patient when mounting and dismounting. A plurality of cushions are mounted for movement along the table to selectably adjustable positions for accommodating patients of different size and shape. The table includes an electrically powered drive system for movement of table components for controlling the different selected working levels for the convenience of a particular chiropractor or other practitioner, the tilting action and cushion position adjustments and a memory is provided in a control system so that table positions and movements for a particular patient and treatment practitioner are automatically repeatable. One or more automatic self-cocking, electrically controlled drops are provided for cushions on the table to initiate automatic lifting and recocking of the drop so that the practitioner can maintain continuous hand contact with the patient being treated while successive drops are performed. The drops automatically measure the patient's weight and provide for a selectively adjustable amount of downward force exerted by the practitioner for initiating a drop of the cushion in a direction selected.

27 Claims, 30 Drawing Sheets

FIG 26
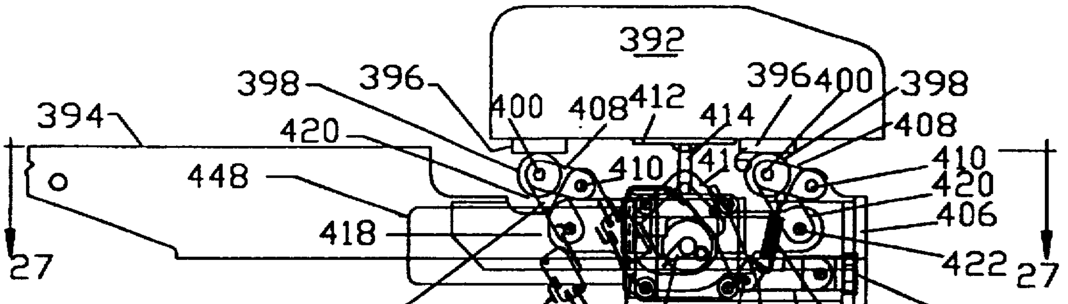
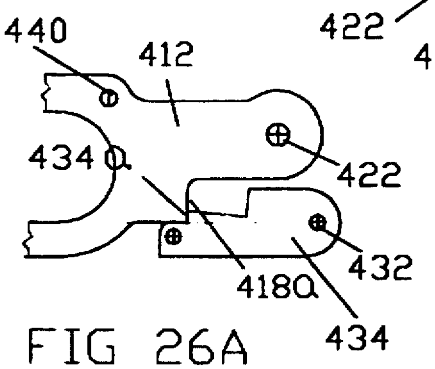
FIG 26A
FIG 27
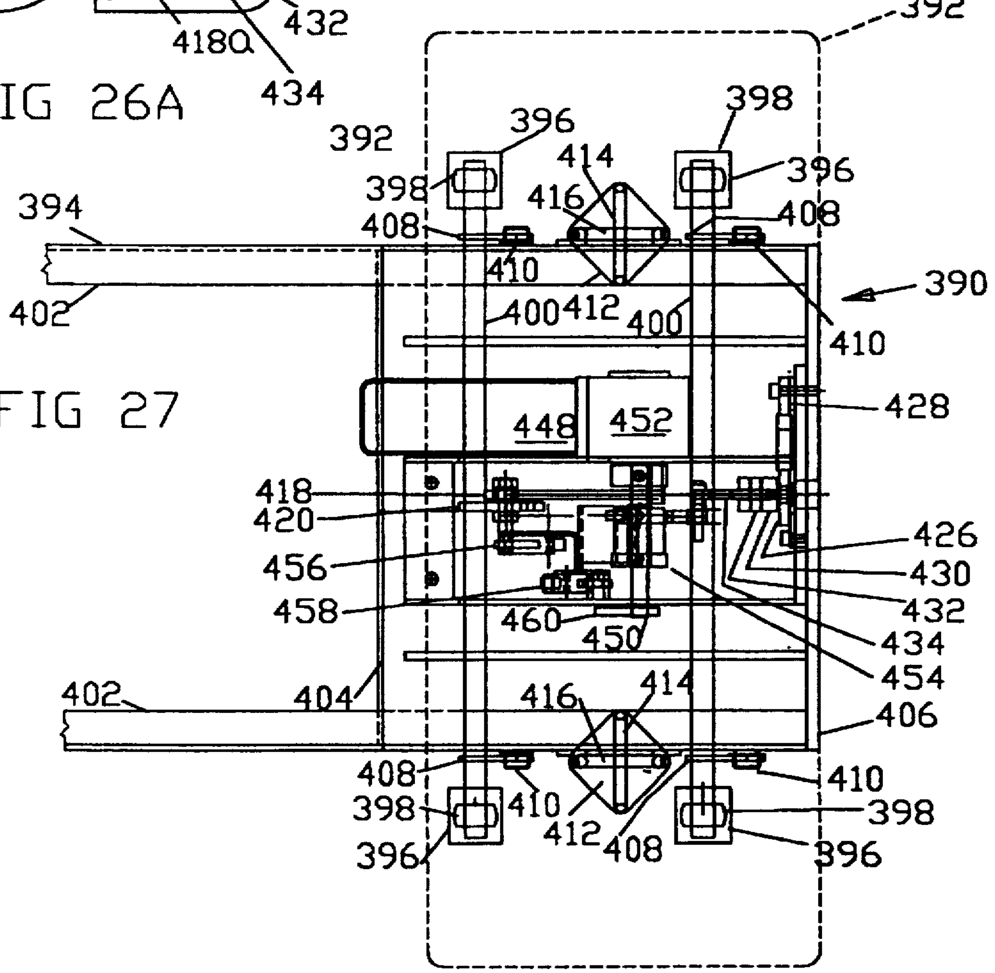

PATIENT TREATMENT APPARATUS

BACKGROUND OF THE INVENTION

1. Field of the Invention

The present invention relates to a new and improved treatment apparatus which is all electric and requires no hydraulic components. More particularly, the treatment apparatus is designed for use by chiropractors and other practitioners and is adapted to accommodate patients of a vast variety of shapes and sizes comprising the 99th percentile of the adult world population including pregnant women and obese persons. The treatment apparatus is designed so that a patient, including patients with physical challenges may easily mount and dismount and the apparatus is designed for use by chiropractors or practitioners of vastly different sizes and strengths. A unique control system is provided having memory capability for moving components of the apparatus to provide repeatable treatment positions for particular patients and for a particular chiropractor or practitioner without requiring additional inputs. A new and unique electrically powered, automatic, self-cocking drop apparatus may be provided for any or all of the patient support cushions and repeated drop treatments are possible without requiring the chiropractor to remove his hand(s) from patient contact between successive drops.

2. Background of the Prior Art

U.S. Pat. No. 3,579,066 discloses a brake motor attachment device including a solenoid mechanically connected to a brake shoe, which upon deactuation of the solenoid automatically engages a brake drum or rotor of an electric motor to stop rotation thereof.

U.S. Pat. No. 3,640,520 discloses a therapy treatment tilt table with a main frame carried by four telescoping legs and a platform pivotally mounted on the main frame.

U.S. Pat. No. 3,806,109 discloses a tiltable treatment table employing hydraulic actuator for tilting a patient support table relative to a base.

U.S. Pat. No. 4,021,028 discloses a tiltable treatment table having a table mounted for pivotal movement relative to a support frame and including a portion tiltable relative to a support frame.

U.S. Pat. No. 4,401,110 discloses a patient treatment table having an upper table frame pivotal to an upright position and movable in a horizontal position to different heights or levels for patient treatment.

U.S. Pat. No. 4,520,800 discloses a patient treatment table having a flexible arch between a hip support board and a head board.

U.S. Pat. No. 4,523,581 discloses a manual chiropractic table cushion drop release mechanism in which frictional drag of a spring biased latch release is removed to provide for a free cushion drop.

U.S. Pat. No. 4,648,389 discloses a patient treatment table having a tuck-away foot board for aiding a patient in mounting and dismounting from the table.

U.S. Pat. No. 4,660,549 discloses an adjustable head support for a chiropractic table which includes a drop mechanism and which is adjustable about an axis generally coextensive with the spinal column and vertebrae of a patient being treated on the table.

U.S. Pat. No. 4,660,817 discloses a multi-step control apparatus for raising and lowering a treatment table in response to predetermined successive motion of the foot of a chiropractor.

U.S. Pat. No. 4,722,328 discloses a chiropractic manipulation table having a system for compensating for the weight of a patient being treated and requiring a relatively uniform amount of vertical force to be applied for flexion distraction of a patient being treated.

U.S. Pat. No. 4,724,554 discloses a tilting patient treatment table having a safety switch mat mechanism for preventing injury to a person as the table is moved between alternate positions.

U.S. Pat. No. 4,850,343 discloses an assist handle for a chiropractic treatment table for aiding a chiropractor in the manipulation of a patient being treated on the table.

U.S. Pat. No. 5,014,688 discloses a patient treatment table having an actuator for pivoting a foot board mechanism and also pivoting the table bed.

U.S. Pat. No. 5,054,142 discloses portable, multi-component contoured, vinyl covered, body support cushions which are independent of one another and are freely movable relative to one another for selective positioning to support a patient during treatment.

U.S. Pat. No. 5,192,306 discloses a chiropractic manipulation table with a flexion/distraction head-piece pivotal about a lateral axis spaced above a thoracic cushion and at or just below a level generally coincident with the patient's spinal axis.

U.S. Pat. No. 5,308,359 discloses an apparatus and method for producing spinal distraction by lifting or rotating a patient's pelvic area and applying a force to the spine for separating vertebrae bodies.

OBJECTS OF THE INVENTION

It is an object of the present invention to provide a new and improved patient treatment apparatus.

It is another object of the present invention to provide a new and improved patient treatment apparatus which is all electrically powered and requires no hydraulic components.

It is yet another object of the present invention to provide a new and improved chiropractic treatment apparatus.

It is still another object of the present invention to provide a new and improved patient treatment apparatus having an adjustment mechanism for a patient's leg length utilizing a telescoping foot support.

It is a still further object of the present invention to provide a new and improved patient treatment apparatus having a power adjustment mechanism for a patient's upper trunk length.

It is another object of the present invention to provide a new and improved patient treatment apparatus having an automatic system providing concurrent table tilting and elevational movement.

It is yet another object of the present invention to provide a new and improved patient treatment apparatus having user programmable elevational settings for different working levels.

It is a still further object of the present invention to provide a new and improved patient treatment apparatus having a foot support with an automatic tilting feature to relieve ankle flexing.

It is an object of the present invention to provide a new and improved patient treatment apparatus including an automatic foot support which is operable to facilitate a patient in mounting and dismounting.

It is yet another object of the present invention to provide a new and improved patient treatment apparatus of the character described in the preceding object which returns to an ankle flexing position for signaling to a patient to dismount from the table.

It is yet a further object of the present invention to provide a new and improved patient treatment apparatus having a foot board movable outwardly to permit a patient leg check test and an automatic return to a latched position prior to patient dismounting.

It is another object of the present invention to provide a new and improved patient treatment apparatus which is capable of providing large elevation changes in working levels yet requiring a relatively small amount of longitudinal table movement.

It is yet another object of the present invention to provide a new and improved patient treatment apparatus having one or more table position indicators utilizing bar codes.

It is another object of the present invention to provide a new and improved chiropractic patient treatment apparatus having an electrically powered, tiltable pelvic support.

It is another object of the present invention to provide a new and improved patient treatment apparatus having a swing away abdominal support movable from a level position to a downward tilt against spring resistance and lockable in position at intervals between an upwardly tilted position and a downwardly tilted position.

It is an object of the present invention to provide a new and improved patient treatment apparatus having a foot operated switch for signaling automatic tilt up to a correct elevation and tilt to a position for conveniently mounting and dismounting.

It is another object of the present invention to provide a new and improved patient treatment apparatus having a tiltable head piece or head support pivotally movable to pivot about a lateral axis at or closely below a patient's spinal column.

It is still another object of the present invention to provide a new and improved patient treatment apparatus having a head piece which is movable between levels above and below a normal elevation.

It is a still further object of the present invention to provide a new and improved patient treatment apparatus having a battery powered system for use when normal electrical power is unavailable.

It is an object of the present invention to provide a new and improved patient treatment apparatus having a main control board and indicators for showing the number of cycles of operation of the table and an error code.

It is another object of the present invention to provide a new and improved patient treatment apparatus having a control system including a foot switch on both sides of the table, conveniently accessible control panels on both sides of the table, indicators on each panel for indicating that a safety factor is at risk, servicing is required and/or maintenance is recommended.

It is yet another object of the present invention to provide a new and improved patient treatment apparatus having a safety system for sensing an obstruction when lowering the table or under the foot board area and automatically stopping table movement and/or raising the table height to clear the obstruction.

It is yet another object of the present invention to provide a new and improved patient treatment apparatus having a safety system for sensing the position of an ankle relaxer and prohibiting table movement until the relaxer is in a retracted condition.

It is a yet further object of the present invention to provide a new and improved patient treatment apparatus having signal means for alerting that the battery back up powered system is in use and/or the battery is low.

It is a further object of the present invention to provide a new and improved patient treatment apparatus having a patient supporting cushion system with adjustably positioned cushions providing comfort zones and generally conforming to body structure of patients of both sexes of all sizes and body shapes.

It is a still further object of the present invention to provide a new and improved patient treatment apparatus having a patient supporting cushion system having molded, single-piece, seamless cushions for easy sanitation and having dual resiliency or density for better patient comfort.

It is an object of the present invention to provide a new and improved patient treatment apparatus having one or more drops which are automatically self-cocking for providing repeated drops without requiring the practitioner to remove his hand(s) from the patient being treated.

It is another object of the present invention to provide a new and improved chiropractic patient treatment apparatus having a drop which automatically weighs the patient and which has an adjustable selector for setting a sensitivity level on the threshold of thrust required to initiate a drop operation.

It is another object of the present invention to provide a new and improved patient treatment apparatus including an improved control system enabling reliable, efficient and effective operations.

It is yet another object of the present invention to provide a new and improved chiropractic patient treatment apparatus which has a drop that is directionally controlled by the thrust vector applied by the chiropractor or practitioner when initiating a drop.

Yet another object of the present invention is to provide a new and improved patient treatment drop apparatus which can be set up for truly vertical drops only, drops restricted to a vertical plane extending longitudinally of the patient's spinal column but angularly adjustable laterally away from the vertical plane toward one side or the other of the patient, and drops restricted to a vertical plane extending laterally of the patient's spinal column but angularly adjustable away from the vertical between head and feet of the patient.

Still another object of the present invention is to provide a new and improved patient treatment drop apparatus providing a drop direction along a downward spiralling path as directed by a practitioner.

BRIEF SUMMARY OF THE PRESENT INVENTION

The foregoing and other objects and advantages of the present invention are accomplished in a new and improved treatment apparatus for supporting a patient lying in a generally prone or a supine position for treatment by manipulation by a chiropractor or other practitioner. The apparatus includes a base and a table supported thereon for movement between selected different horizontal positions or working levels. The table is also tiltable toward and away from an upright position for facilitating the patient in mounting and dismounting before and after treatment and includes a foot piece adjacent an end of the table for supporting the patient when mounting and dismounting. A plurality of cushions are mounted for movement along the table to selectably adjustable positions for accommodating patients of different size and shape. The apparatus includes an electrically powered drive system for movement of table components for controlling the different selected working levels, the tilting action and cushion position adjustments and a memory is provided in a control system so that table positions and movements for a particular patient and a particular chiropractor are automatically repeatable. One or more automatic self-cocking, electrically controlled drops are provided for the cushions on the table to initiate automatic lifting and recocking of the drop so that the chiropractor can maintain continuous hand contact with the patient being treated while successive drops are performed. The drops automatically measure the patient's weight and provide for a selectively adjustable amount of downward force or thrust exerted by the chiropractor for initiating a drop of the cushion in a direction as selected by the chiropractor.

BRIEF DESCRIPTION OF THE DRAWINGS

For a better understanding of the present invention, reference should be had to the following detailed description taken in conjunction with the drawings, in which:

FIG. 26 is a side elevational view of a typical drop mechanism for the apparatus shown in a cocked or latched elevated position ready for a drop operation;

FIG. 26A is an enlarged fragmentary side elevational view showing a latch of the drop mechanism in a latched position;

FIG. 27 is a plan view of the drop mechanism looking downwardly in the direction of arrows 27—27 of FIG. 26;

FIGS. 49A, 49B and 49C together provide a flow chart illustrating an operating process of the patient treatment apparatus.

DETAILED DESCRIPTION OF A PREFERRED EMBODIMENT OF THE INVENTION

Figure 1:
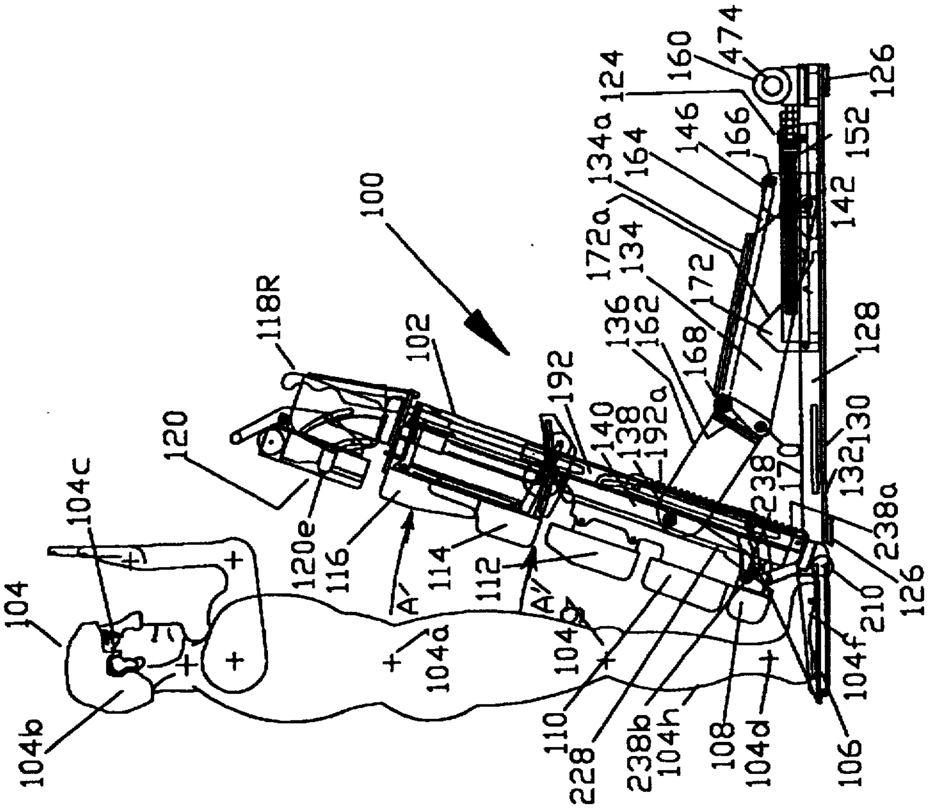
FIG. 1 is a side elevational view of a new and improved chiropractic treatment apparatus constructed in accordance with the features of the present invention and shown with a relatively tall patient approaching for treatment and standing on a foot board of the apparatus.

Referring now more particularly to the drawings, in FIGS. 1–9 is illustrated a new and improved patient treatment apparatus 100 constructed in accordance with the features of the present invention. The apparatus 100 includes an elongated table 102 designed to support a patient 104 for treatment by manipulation while lying in a generally horizontal prone position face down as illustrated in FIGS. 6–9 or in a supine position when desired.

To aid a patient 104 in mounting and dismounting, the table 102 is pivotal between an upright position (FIGS. 1–4) having an upward slope of approximately 70° relative to the horizontal and a horizontal or other sloping treatment position. The apparatus 100 includes a foot board or support 106 onto which the patient 104 steps initially when mounting and the foot board or foot piece also provides for patient support during pivotal movement (FIG. 5) of the table 102 intermediately between the upright, near vertical, position and a horizontal or other treatment position.

The patient 102 is supported on a plurality of resilient cushions including an ankle rest 108 at a lower or foot end of the table 102 adjacent the foot board 106, a knee cushion 110, a pelvic support cushion 112, an abdominal support cushion 114, a breast or thoracic support cushion 116, a pair of arm rests 118L and 118R (FIGS. 11A, 11B, 11C) and a head supporting structure or head piece 120 at the head or front end of the table. The cushions are movable on the table structure relative to one another in order to accommodate patients of widely ranging weights, sizes and shapes, as will be discussed hereinafter in connection with FIGS. 9 and 11A, 11B and 11C.

The apparatus 100 is capable of handling patients of widely varying weights, sizes and shapes so as to accommodate all adult people within the 99th percentile of the earth's population. Referring to FIG. 1, when a particular patient 104 (for example, one who is six feet tall) is to be treated and is standing on the foot board 106 supported on the floor, the patient's ilia **104*a* (i.e., top of the pelvic bone) may be at a level (arcuate line A) above the level (arcuate line A') of the upper edge of the pelvic cushion 112 when the table 102 is in a retracted or minimum length condition as shown. The height of the pelvic cushion 112 is then raised upwardly above the foot board 106 until an upper end of the pelvic cushion 112 is in proper position (FIG. 2, arcuate lines A and A' substantially coincide) to accommodate the particular patient's leg length. This upward movement of the pelvic cushion 112 is accomplished by movement of the table 102 upwardly to the desired level while the foot board 106** remains on the floor as will be described in detail hereinafter.

Figure 2:
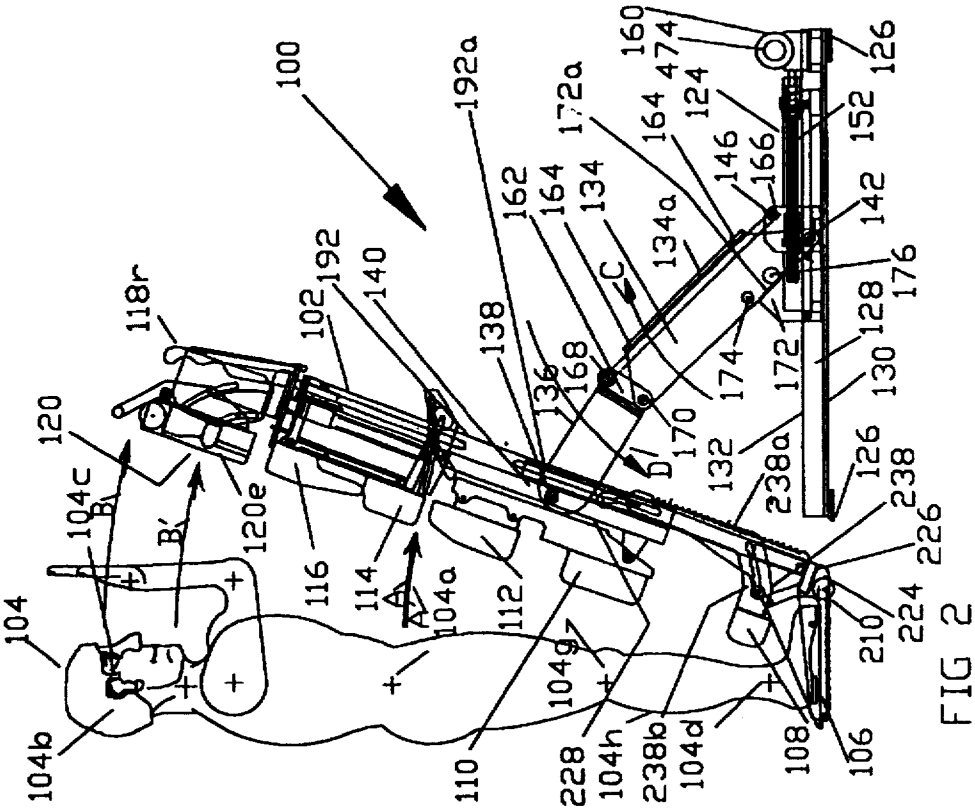
FIG. 2 is a side elevational view of the apparatus after adjustment of a pelvic support section to match the pelvic height of the patient.

As shown in FIG. 2, after the table 102 is elevated to accommodate the leg length of the patient 104, the head piece 120 may still be at a height level below that desired for proper support of the patient's head **104*b* as indicated by the space between the arcuate line B at patient's eye level 104*c* and the arcuate line B' at the level of an eye opening 120E in the head piece. The head piece 120 is then moved outwardly of the table structure until the arcuate lines B and B' substantially coincide (FIG. 3) ensuring that the patient's face and head are properly supported. During this time, the arm rests 118L and 118R and the breast or thoracic cushion 116 move collectively along with the head piece 120 away from the abdominal cushion 114**.

After the apparatus 100 has been adjusted to accommodate the leg length and eye level height of a particular patient 104 as described, the patient 104 leans forwardly (FIG. 4) to contact the cushion surfaces and grasp the hand holds on the arm rests 118L and 118R as shown. As will be described hereinafter, the apparatus 100 may include an electronic memory device which stores patient data for a particular patient so that the leg height and eye level height adjustments are accomplished automatically when a patient identifying code is entered.

Figure 4:
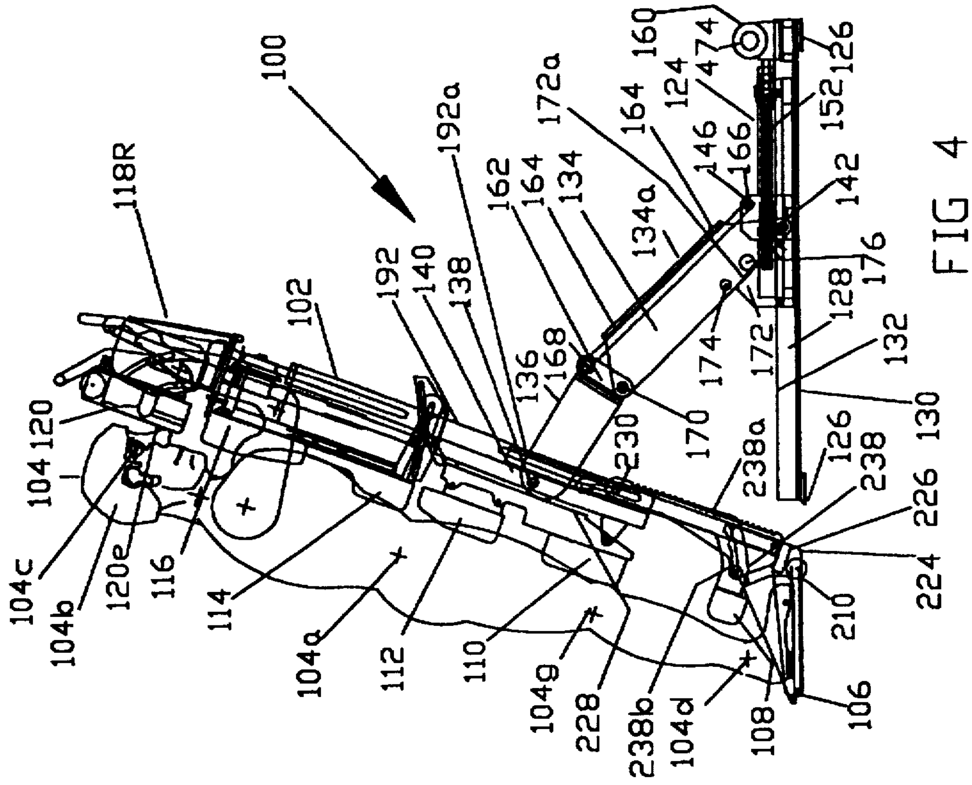
FIG. 4 is a side elevational view of the apparatus shown with the patient's ankles flexed and leaning against the adjusted support section ready for tilting movement thereof toward a horizontal position for treatment.
Figure 5:
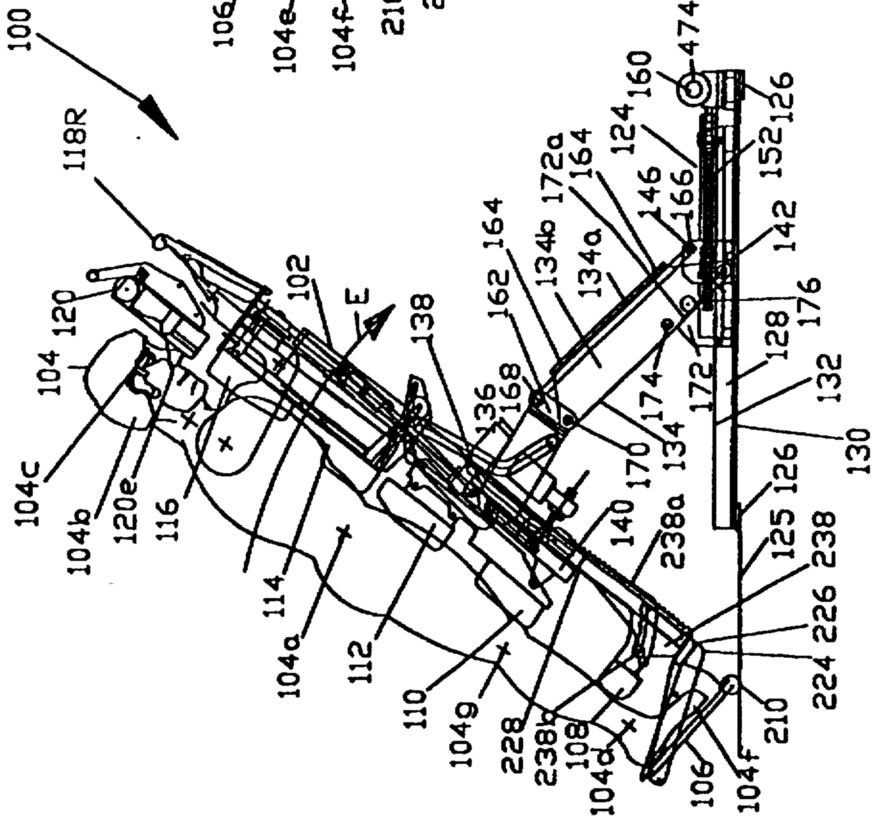
FIG. 5 is a side elevational view of the apparatus shown in an intermediate tilted position moving toward a horizontal treatment position and the foot has pivoted to relieve ankle flex.

Once the patient 104 is leaning against the cushions as shown in FIG. 4 with ankles **104*d* flexed, the table 102 is rotated in a clockwise direction or tilted downwardly from the upstanding 70° position toward a horizontal position as indicated in FIG. 5. As the down-tilting action proceeds, the patient's ankle flexion (FIG. 4) is relaxed and the foot board 106 rotates relative to the table 102 to become normal thereto against the soles 104***e* of the patient's feet 104*f* as indicated in FIGS. 6, 7, 8 and 9. When a horizontal or other sloping treatment position is reached, the patient's legs are also supported on the ankle rest 108.

Figure 10A:
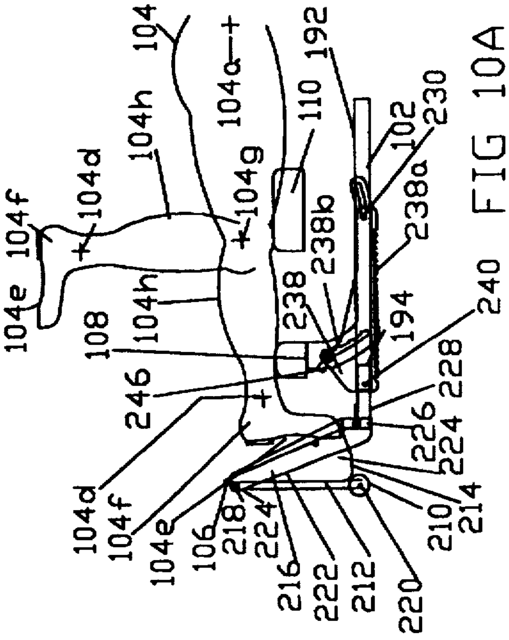
FIG. 10A is a fragmentary elevational view of a foot end portion of the apparatus showing a leg check latch in a released position with the foot board moved out to permit a leg check test of the patient.
Figure 10B:
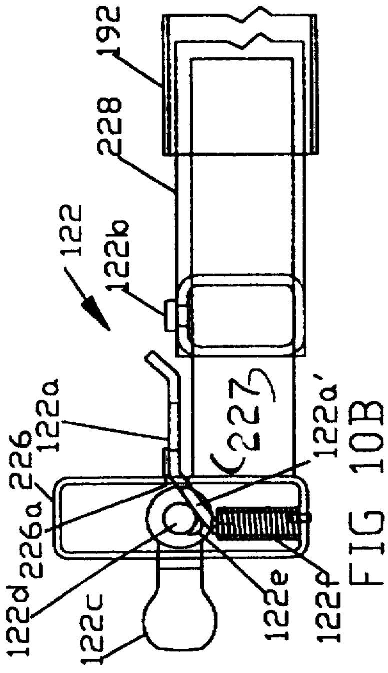
FIG. 10B is an enlarged fragmentary side elevational view of the leg check latch.
Figure 9:
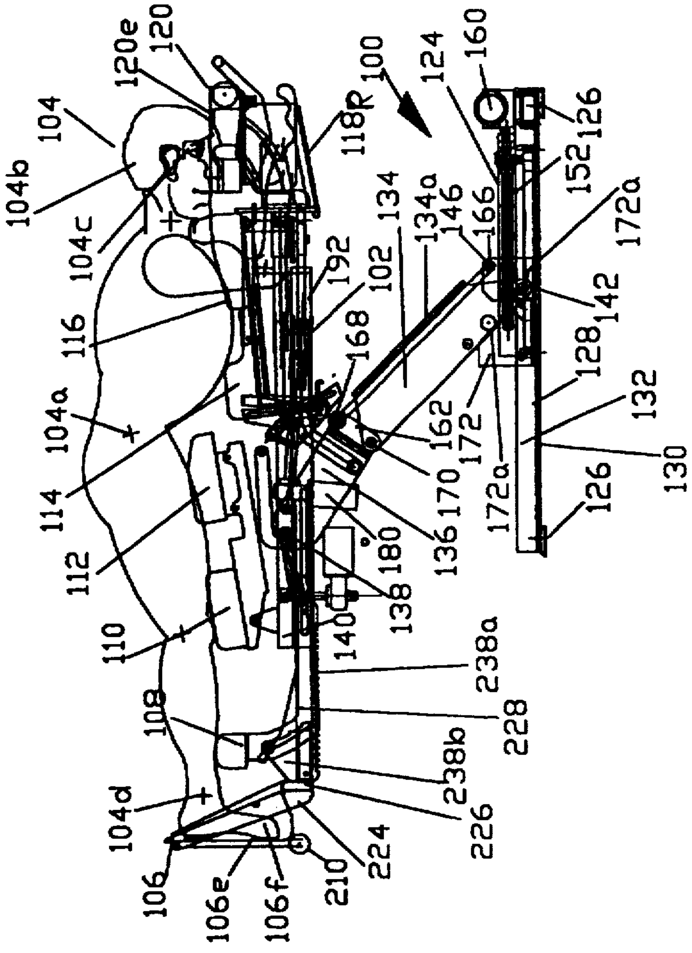
FIG. 9 is a side elevational view of the apparatus showing the pelvic support section in an upwardly tilted position.

If a leg check test is desired requiring the patient's leg(s) to be pivoted at the knees 104*g* so that the calves 104*h* extend upwardly as shown in FIG. 10A, a leg check latch system 122 (FIG. 10B) may be released permitting the foot board 106 to be moved farther out away from the patient's feet.

A releasable latch 122*a* is engageable with a restraining pin 122*b*, mounted on the cross member 226 and a knob 122*c* mounted on a rotatable pivot shaft 122*d* in the cross member is rotated in a counterclockwise direction to effect a release. An actuating pin 122*e* rotates with the shaft 122*d* for depressing an inside end 122*a*' thereof downward against a compression spring 122*f*. Downward movement of the end 122*a*' causes the latch 122*a* to rotate in a slot 226*a* provided in the cross member 226. This rotation lifts an outer end of the latch 122*a* above pin 122*b* allowing a practitioner to pull the footplate 212 outwardly away from patient's feet 104*f*.

The footplate 212 may be relatched by a practitioner upon pushing footplate inward until the latch 122*a* reengages the pin 122*b*. Alternately, the footplate 212 will automatically relatch when the rollers 220 contact the floor 125 during tilt up operation of the table 102.

In accordance with the present invention, the table 102 is supported from a floor 125 (FIG. 5) or other surface on a rectangular-shaped, elongated base 124 having outrigger feet 126 at opposite ends which can be permanently fastened in place on the floor. The base 124 includes a rigid but relatively small-in-area, metal base channel 128 having a bottom or web 130 and a pair of integral, upstanding side flanges or guide walls 132 along opposite longitudinal edges.

Figure 16:
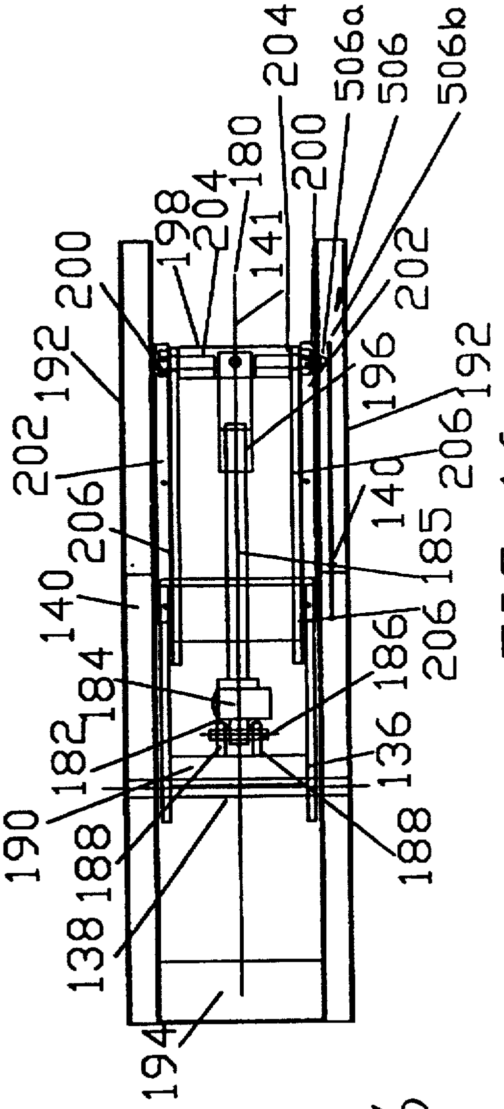
FIG. 16 is a top plan view of the table tilt drive mechanism taken substantially as looking in the direction of arrows 16—16 on FIG. 15A.
Figure 17:
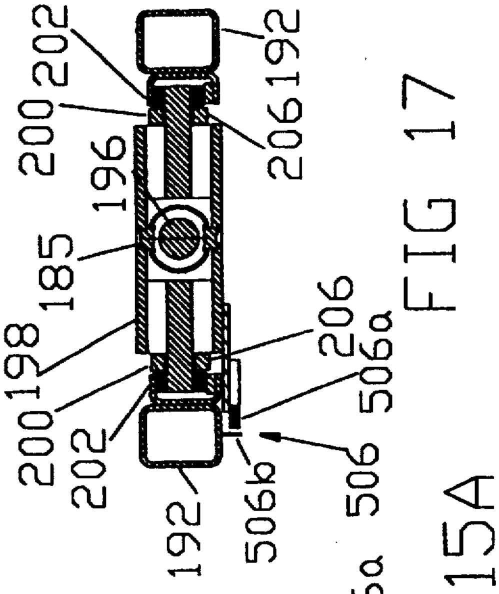
FIG. 17 is a transverse cross-sectional view of the table tilt drive mechanism taken substantially along lines 17—17 of FIG. 15A.
Figure 15B:
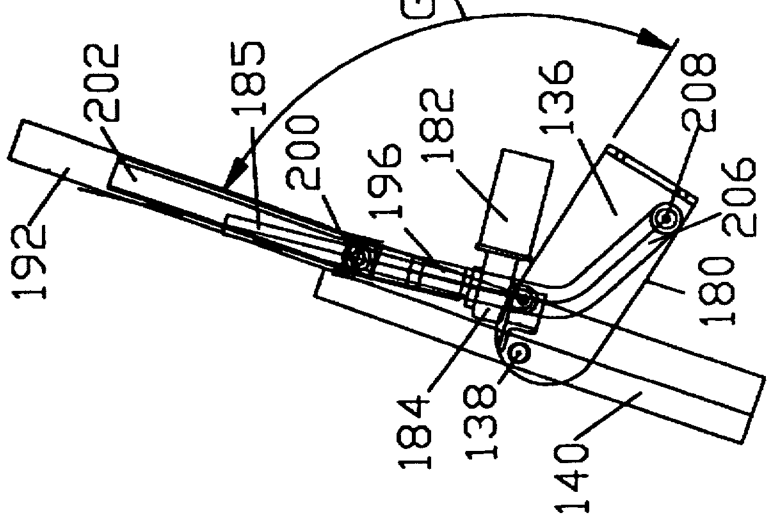
FIGS. 15A and 15B are schematic side elevational views of an electrically powered table tilt drive mechanism of the apparatus showing the tilt mechanism with the table in a horizontal position and a fully tilted position, respectively.
Figure 15A:
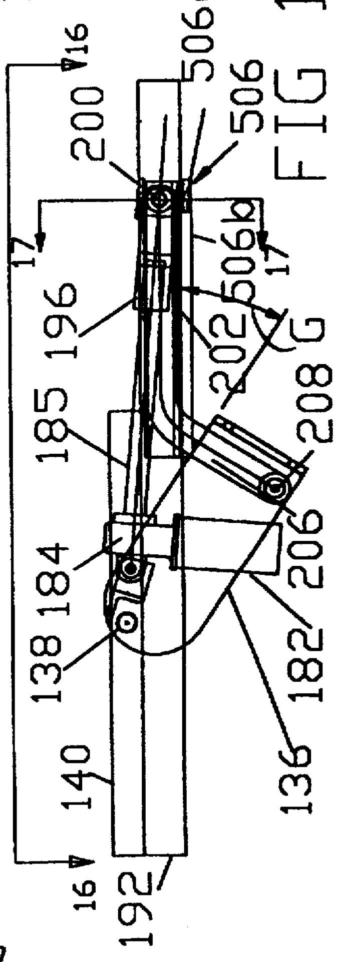

A table support column 134 of rigid metal is supported for longitudinal and pivotal movement relative to the base channel 128 and a support leg 136 of shorter length is detachable connected to an outer or free end portion of the support column. The support leg 136 is pivotally interconnected to the table 102 intermediate its length by a table tilt cross pin or axle 138 extending transversely between a pair of parallel, hollow tubular side frame members 140, as best shown in FIGS. 15A and 16.

Figure 13:
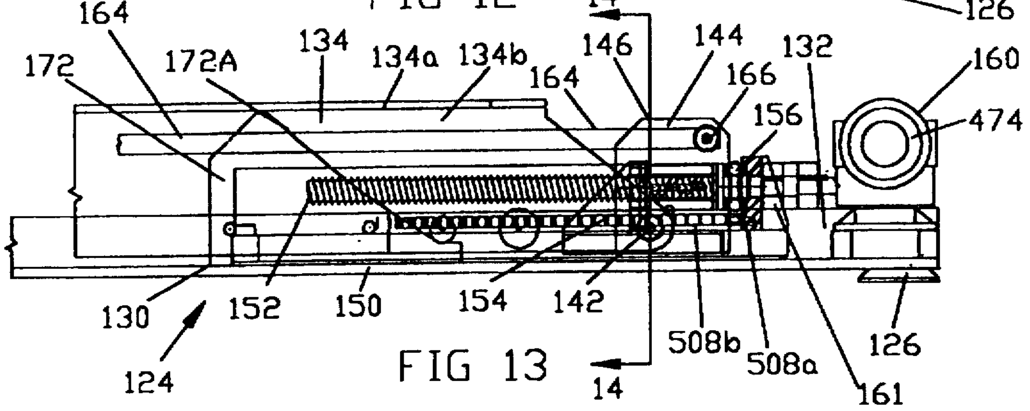
FIG. 13 is a side elevation view of the elevation drive mechanism.
Figure 14:
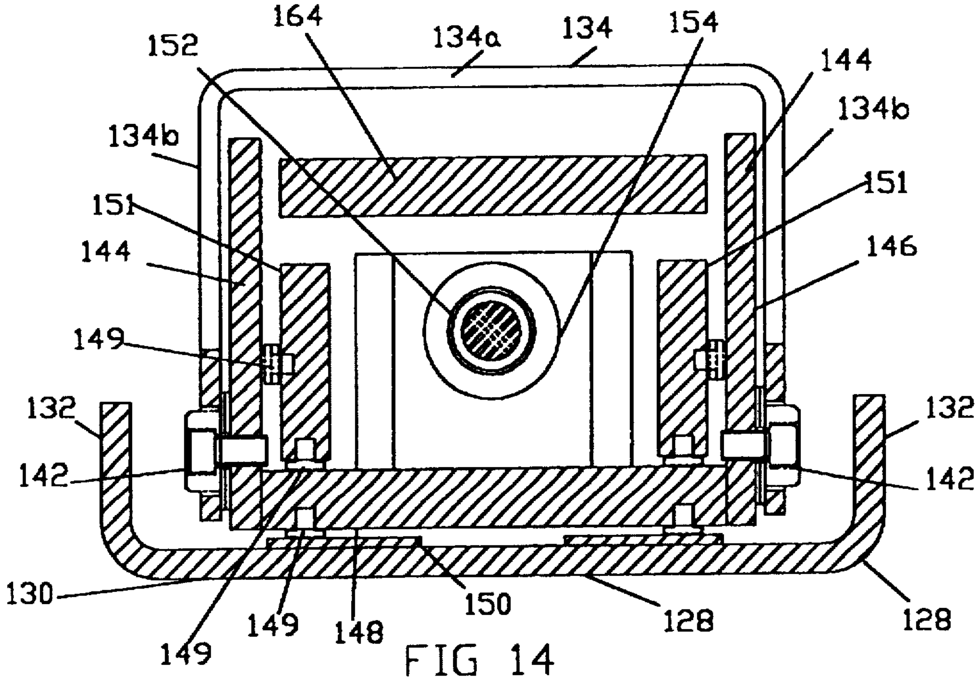
FIG. 14 is a cross-sectional view of the elevation drive mechanism taken substantially along lines 14—14 of FIG. 13.

The support column 134 is of channel-shaped transverse cross-section including a top wall or web 134*a* and a pair of opposite, longitudinally extending, integral side flanges 134*b*. A lower corner at the head end of the side flanges 134*b* is connected by pivot pins 142 to opposite, parallel side members 144 of a pusher block assembly 146. The pusher block assembly 146 is movable longitudinally along a central axis of the base channel 124 between a starting or head end portion (FIGS. 1, 8 and 13) and various activated positions along the length of the base channel 128 as shown in FIGS. 2–7 and 9, the opposite side members 144 of the pusher block assembly 146 are attached to opposite side edges of a base plate 148 which slides along low friction guide pads 149 which rest on strips 150 provided on the upper surface of the channel bottom 130. The low friction pads 149 are placed in upper guide bars 151 to restrain the pusher block 146 from side or upward motion.

Controlled movement of the pusher block assembly 146 to selected positions along the base channel 128 is achieved by a rotating threaded jack screw 152 engaged in a thread bore provided in a ball screw nut 154 carried on the pusher block assembly 146. Rotation of the jack screw 152 in one direction causes the pusher block assembly 146 to move away from the head end of the base channel 128 toward the opposite end and rotation of the jack screw in an opposite direction results in movement of the pusher block assembly back toward the head end of the base channel.

The head end of the jack screw 152 is supported in a thrust bearing assembly 156 carried on a thrust bracket 158 fixedly attached to the base channel 128. Power for rotating the jack screw 152 to move the pusher block assembly 146 and column 134 longitudinally of the base channel 128 is provided by a reduction gear box 158 and a reversible, elevation controlling, electric motor 160 mounted at the head end of the base channel. The jack screw 152 is connected to the gearbox 158 by a flexible coupling 161. By providing a drive control signal to the elevation motor 160 the position of the head end of the support column 134 relative to the channel base 128 is precisely controlled as selected and the position is pre-programmed electrically for repeated performance for a particular patient being treated. An elevation position indicator 508, preferably including a reader 508*a* and a bar coded strip 508*b* provides position information for indicating the position of the head end or bottom of the column 134 along the base channel 128. A brake 474 is provided to maintain or retain the position of the support column 134 on the base channel 128 after stopping or deenergizing the motor 160 until the motor is again energized, at which time the brake is released.

Figure 12:
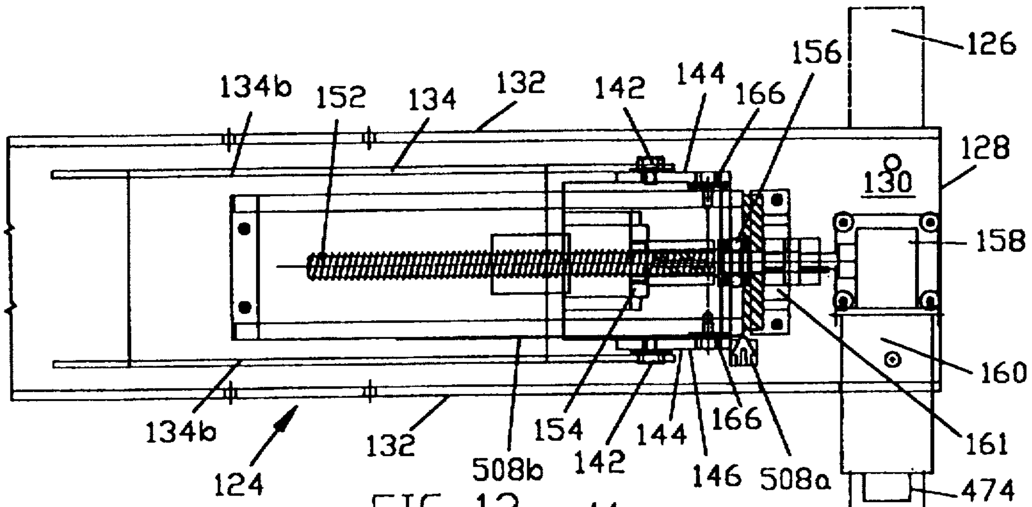
FIG. 12 is a top plan view of an electrically powered elevation drive mechanism of the apparatus.

As illustrated well in FIG. 4, a parallelogram-type linkage is provided between the standing pusher block assembly 146 and a base connection 162 located between the free or foot end of the support column 134 and the adjacent end of the support leg 136. An upper thrust bar 164 positioned between the opposite side flanges 134*b* of the support column 134 is pivotally connected at a head end of upper head end corner portions of the side members 144 of the pusher block assembly 146 by means of pivot pins 166 (FIGS. 12 and 13) and an opposite end of the thrust bar is pivotally connected to the base connector 162 by pivot pins 168. A lower portion of the side flanges 134*b* to the support column provides a lower linkage parallel to the upper thrust bar 164 and of equal length extending between the pivot pins 142 at a head end portion and another lower support leg cross pin 170 at the free or foot end portion.

In accordance with an important feature of the invention, as the pusher block assembly 146 is moved away from the head end of the base channel 128 from right to left as depicted in FIGS. 1 and 2, the support column 134 moves in the same direction in a horizontal sense but at the same time begins to pivot upwardly in a clockwise direction (Arrow C, FIG. 2) about a pivot axis coincident with the pivot pins 142. Because of the parallelogram linkage previously described, the support leg 136 begins to pivot in a counterclockwise direction (Arrow D, FIG. 2) relative to the support column 134 about the axis of the cross pin 170.

Pivotal movement of the support column 134 from a horizontal position (FIG. 8) when the pusher block assembly 146 is adjacent the head end of the base channel 128 in a clockwise direction toward an upwardly sloping position as shown in FIGS. 1–7 and 9 as the pusher block assembly is moved away from the head end of the base channel by rotation of the jack screw 152 in one direction is attained by means of a pair of cams 172 having upwardly sloping curved cam surfaces 172*a* (FIG. 13) mounted on the channel base on opposite sides of the support column side flanges 134*b*.

The cam surfaces 172*a* are first engaged by small cam follower rollers 174 and then by larger diameter cam follower rollers 176 on opposite sides of the support column 134. The slope, position and curvature of the cam surfaces 172*a* are chosen to provide the desired amount of support column 134 pivoting action in relation to movement of the head end of the column away from the elevation drive motor 160 along the base channel 128.

The cam surfaces 172*a* are located approximately midway between opposite ends of the base channel 128 and are first engaged by the smaller cam follower rollers 174 (FIG. 1) with the table 102 in a contracted condition and the foot board 106 resting on the floor awaiting arrival of a patient 104. The table 102 may then be moved upwardly to the position of FIG. 2 to accommodate the pelvic height and eye level height of a particular patient 104 as previously described, by right to left movement of the pusher block assembly 146. This movement causes the support column 134 to pivot in a clockwise direction (Arrow C) as the smaller cam follower rollers 174 move above the cam surfaces 172*a* which are now engaged by the large diameter rollers 176. As this movement occurs, the support leg 136 pivots in a counterclockwise fashion (Arrow D) permitting the table 102 to move upwardly of the foot board 106 while maintaining approximately the same angle of tilt of approximately 70°.

Figure 6:
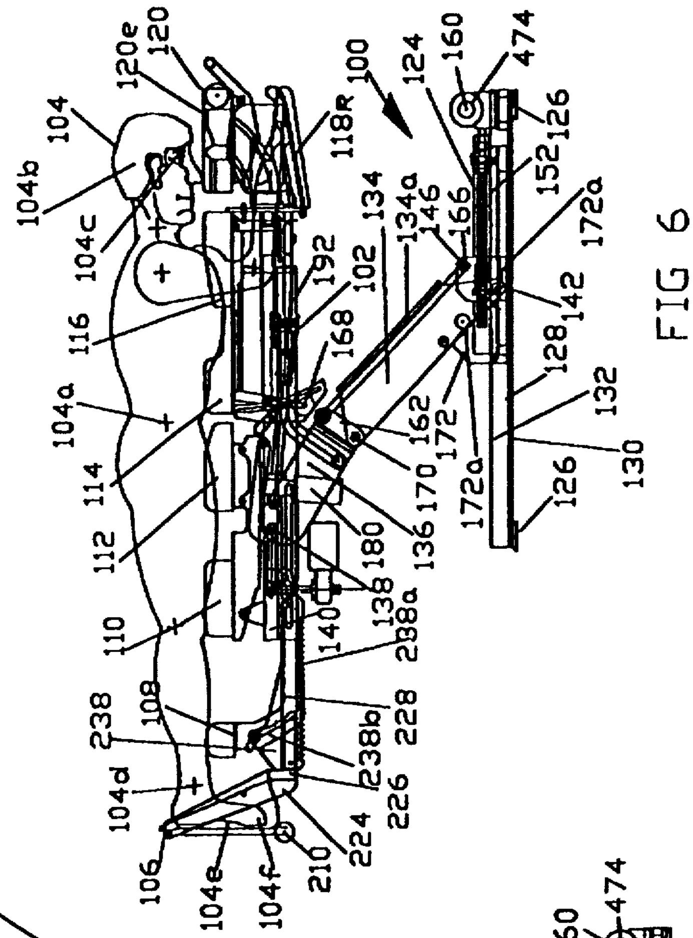
FIG. 6 is a side elevational view of the apparatus in a horizontal treatment position at a selected intermediate level ready for treatment of the patient.

After the table cushion sizing has been completed (FIG. 3), the patient 104 leans forward to engage the surfaces of the cushions 108, 110, 112, 114, 116 and head piece 120 as shown in FIG. 4. Thereafter as depicted in FIG. 5, the table 102 is tilted in a clockwise direction (Arrow E, FIG. 5) to pivot toward a horizontal treatment position as shown in FIG. 6. Depending on a chiropractor's choice of a conventional working level for treating the patient 104, as the table 102 tilts toward the horizontal treatment position at a selected level (FIGS. 6, 7 and 8) the support column 134 may remain in the same elevated position tilted position (FIG. 6) as in the tilt commencing position of FIGS. 4 and 5 or may be tilted upwardly in a clockwise direction (Arrow F, FIG. 7) to a more upright position for a higher working level by movement of the pusher block assembly 146 further to the left by the jack screw 152. When a minimum elevation treatment position is desired as shown in FIG. 8, the pusher block assembly 146 may be returned to the right to a starting position adjacent the elevation motor 160.

Figure 7:
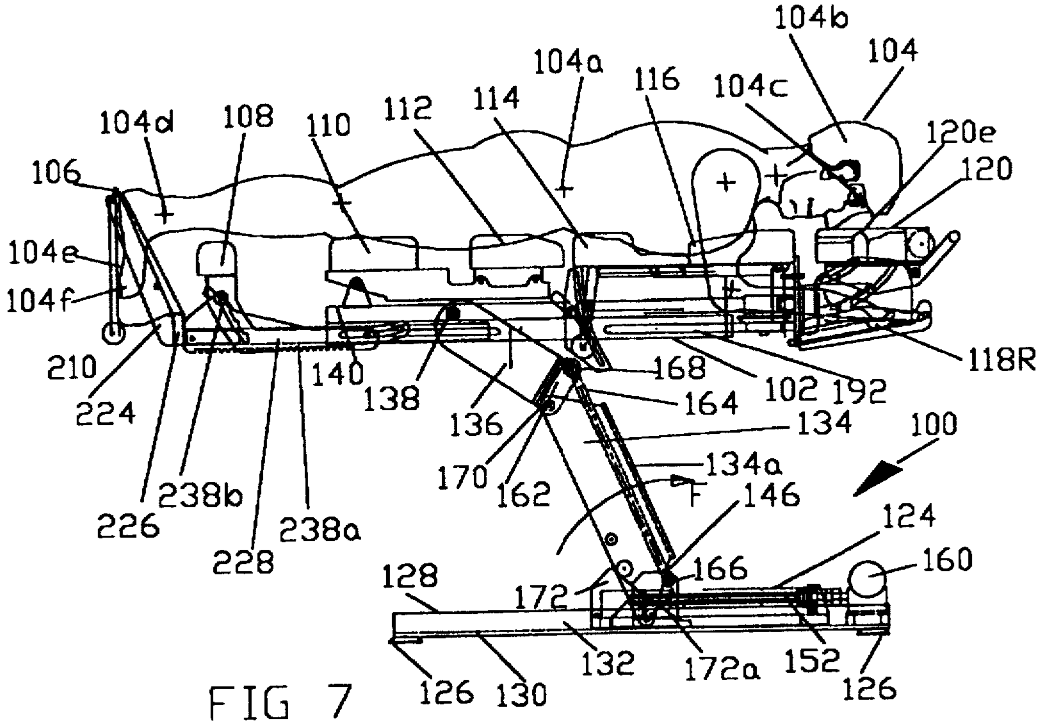
FIG. 7 is a side elevational view of the apparatus in a relatively higher level horizontal treatment position for accommodating a relatively tall practitioner.
Figure 8:
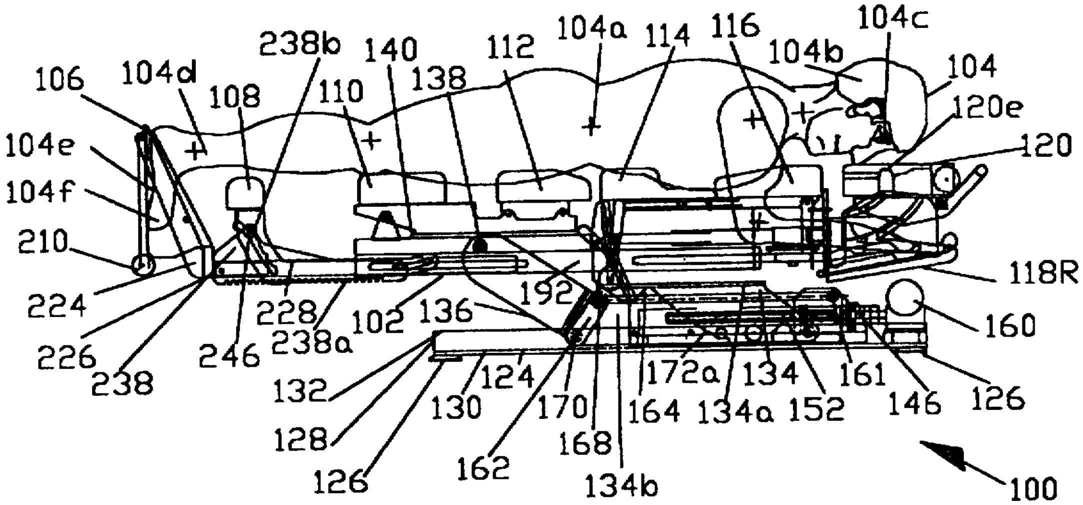
FIG. 8 is a side elevational view of the apparatus in a relatively lower level horizontal treatment position for accommodating a relatively short practitioner.

During the pivotal movements of the support column 134 as just described, the relative angle between longitudinal axes of the support column and the support leg 136, respectively, is changed to maintain the table 102 in a continuing horizontal or treatment position even though the height or level above the floor 125 is changed to suit or accommodate a particular patient and chiropractor (FIGS. 6, 7 and 8). This feature is accomplished by the unique parallelogram linkage as described, the unique cam system and the variable electrically controlled positioning of the pusher block assembly 146 on the base channel 128 as movements occur.

In addition, the relative angle between the table 102 and the support leg 136 pivotally connected thereto is variable and controlled by a table tilt control system 180 best shown in detail in FIGS. 15A, 15B, 16 and 17. The table tilt control system 180 is powered by a reversible, electric motor 182 acting through a right angle reduction gear box 184 to drive an elongate jack screw 185 aligned along a central axis 141 of the table 102 midway between the hollow tubular side frame members 140 and transverse to the table tilt pin or axle 138 extended therebetween (FIG. 16).

The gear box 184 is pivotally supported by a cross pin 186 extending through a pair of brackets 188 attached to an angle cross-member 190 extended transversely between the side frame members of the support leg 136. Each side frame member of the side frame tube 140 rests on and supports a lower, hollow, tubular elongated side frame member 192 of the table 102, projecting toward the head end of the table beyond the head end of the frame member 140 as best shown in FIGS. 15A and 15B. At a foot end portion of the elongated hollow tubular frame members 192, a cross-member 194 is provided to form a strong rectangular frame structure of the table 102 for supporting the cushions and a patient 104 lying thereon.

An outer end portion of the jack screw 186 is threadedly engaged in a hollow internally threaded sleeve 196 which is supported on a transverse member 198 having rollers 200 at opposite ends adapted to roll in channel tracks 202 (FIG. 17) attached to the inside facing walls of the table side frames 192. Each roller 200 is mounted on an axle 204 supported to extend outwardly of the end of the cross-member 198. Between each opposite end of the cross-member 198 and the adjacent roller 202 there is sandwiched a head end portion of a generally L-shaped link 206 having a down-turned foot end portion pivotally interconnected to the support leg 136 with axle pins 208. A force triangle is formed between the table axle pin 138, the axle pins 208 and the roller axle 204 and as the distance between the pins 208 and axles 204 is changed by operation of the jack screw 185 the angular relationship between the table 102 and the support leg 136 is changed.

As viewed in FIG. 15A, when the table 102 is in a horizontal position, the support leg 136 is positioned relative to the table 102 at a relatively shallow angle G and the jack screw driven cross-member 198 is at the head end of the roller tracks 202. When the table 102 is in a 70° tilted or upright position for patient mounting and dismounting (FIG. 15B) the angle between the table and support leg is a much larger obtuse angle G'. It is thus seen that the electric elevation motor 160 and the tilt motor 182 are used precisely to control the amount of elevation of the table 102 above the floor 125 and the angle of tilt of the table relative to the floor. Moreover, these electric motors are operated by predetermined programmed control to provide the desired table positions selected and stored in memory for different patients 104 and different chiropractors or practitioners specifically.

It should also be noted that the elevation motor 160 and the table tilt motor 182 cooperate with the parallelogram linkage system as described and with the cams 172 to ensure that the overall center of gravity of the table 102 with or without a patient 104 thereon, remains within a restricted dimension relative to the base channel 128 so that there is no tendency of the apparatus 100 to tip over or be unstable during patient mounting and dismounting and during table elevation and lowering, even though an extremely wide range of tilt angles from horizontal to 70° upright and an extremely wide range of working levels from 18" to 38" above the floor level are provided. Moreover, this versatility is accomplished with a minimum length base size and a minimum length table size so that the floor space required in a practitioner's office is minimal.

In FIG. 1, the table 102 is shown in an upright, 70° tilt position ready for receiving a new patient 104 who steps onto the foot piece 106 which rests on the floor 125. In this position the support column 134 is in a slightly tilted position and the pusher block assembly 146 has been moved a short distance along the base channel 128 away from the motor 160 by the jack screw 152. The support leg 136 is in a position tilted slightly upwardly relative to the support column 134, and the foot end of the table 102 is close to the level of the floor.

In order to elevate the table 102 so that the pelvic cushion 112 is raised to the level of the patient's ilia 104*a* (i.e., to accommodate the patient's leg length), the support column 134 is driven by the jack screw 152 and motor 160 further down the base channel 128 away from the motor end and this causes the support column to begin tilting further upward to the position shown in FIG. 2 as the rollers 174 and 176 ride up on the elevating surface 172*a* of the cams 172. As this movement takes place, the parallelogram linkage between the support column 134 and support leg 136 causes the support leg to pivot downwardly in a counterclockwise direction as the support column pivots upwardly in a clockwise direction, thus permitting the table 102 to be moved upwardly while the 70° upstanding tilt position remains the same.

Figure 3:
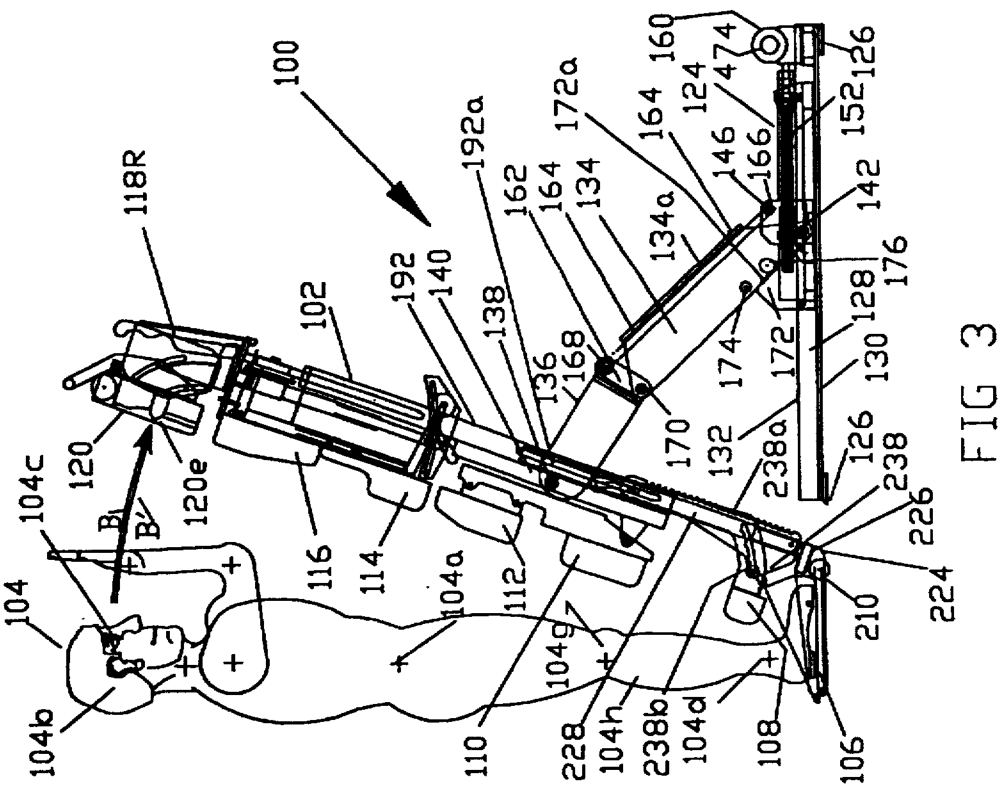
FIG. 3 is a side elevational view of the apparatus after adjustment of a front section to align a head support section with the eyes of the patient.

After the head piece 120 is adjusted to match the patient's eye level as shown in FIGS. 3 and 4 and it is desired to pivot the table 102 in a downward direction (FIG. 5) toward a horizontal position (FIG. 6), the table tilt motor 182 is energized causing the support leg 136 to pivot in a counterclockwise direction relative to the support column 134 until the table 102 is in a horizontal position. Thereafter, raising and lowering of the horizontal table 102 to higher (FIG. 7) and lower (FIG. 8) positions to provide a most convenient working level for a particular practitioner (short or tall) and a particular patient (thick or thin body) is accomplished by moving the lower support column 134 to a more upstanding position (FIG. 7) with the pusher block assembly 146 being spaced farther down the base channel 128 away from the motor or a shallower tilt angle by movement of the pusher block assembly back toward the motor end of the base channel. A tilt position indicator 506 is provided on the table 102 including a reader 506*a* and a bar code strip 506*b*.

After treatment is completed, the table 102 is returned to a generally mid level height by the controlled operation of the elevation motor 160 as shown in FIG. 6 and the tilt motor 182 is energized to cause the support leg 136 to pivot in a clockwise direction relative to the table about the pin 138. This action causes the table 102 to approach (FIG. 5) the 70° upright tilt position (FIGS. 1–4) so that when the foot board 106 reaches the floor surface 125, the patient 104 can step off or dismount.

Overall, the footprint area required for the apparatus 100 in an office of a chiropractor or other practitioner is small in comparison to other tables or treatment apparatus used heretofore because of the unique concurrent or simultaneous movement between the table 102, the support leg 136 and the support column 134 relative to the base channel 128. Movement of the support column 134 along the base channel 128 and the changing slope angle relative to the base channel concurrently while the angle between the support leg 136 and the support column is changing, and while the angle between the support leg and the table 102 is also changing, results in a very stable apparatus 100 during operation with a minimum footprint or floor space area requirement.

It should further be noted that the apparatus 100 requires no hydraulic systems. The apparatus 100 includes repeatable, pre-programmed, precise control for accommodating patients of extreme size (both large and small), extreme variations in weight (from a child to a 300–400 pound patient 104) and extremely different body shapes (varying between thin to obese, to pregnant, to deformed, to male and to female, and the like).

In accordance with the present invention, the foot board 106 is telescopically attached and supported from the table 102. When a patient 104 is mounting or dismounting as in FIGS. 1–5, the foot board or support piece 106 is partially supported from the floor surface 125 on a plurality of rollers 210 provided at the toe end of the foot board. When the table 102 is tilted toward the horizontal FIGS. 5–9, the foot board rollers 210 move then leave the base channel 128 and away from the floor surface 125 so that the foot piece 106 reaches a vertical position when the table 102 is in a horizontal position.

The foot board 106 (FIG. 10) includes a foot plate 212 and an integral upstanding toe plate 214 and the foot plate is mounted on side support frame members 216 having an axle pin 218 at the open end and a roller axle 220 at the toe end carrying the rollers 210. At opposite sides, the foot board is provided with generally triangular-shaped side plates 222 secured to the frame members 216 along a lower edge and to the opposite ends of the foot plate 212 and the toe plate 214 to form a containing but open-ended enclosure for the patient's feet 104*f*.

Figure 19:
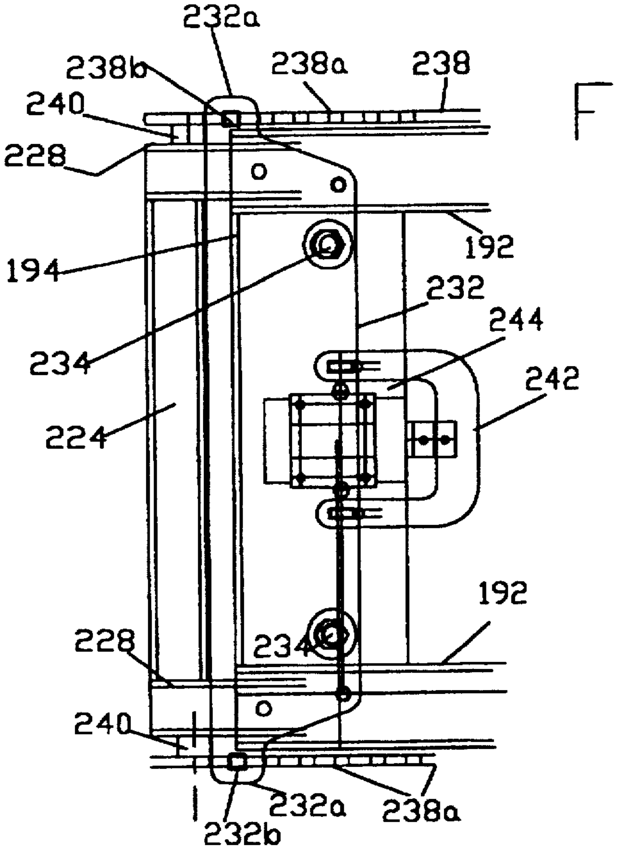
FIG. 19 is a bottom view of the foot board control and latch mechanism looking in the direction of arrows 19—19 of FIG. 18.

On opposite sides, the side plates 222 are supported by hollow tubular arms 224 having an outer end portion supporting the open end axle 218 and toe end joined to a hollow tubular cross-member 226 of generally rectangular transverse cross-section, best shown in FIGS. 10 and 19. The cross-member 226 is joined at opposite end portions to the outer ends of a pair of rectangular bars 227 that telescopically slide in hollow tubular support legs 228 which are mounted for telescopically adjustable slidable movement in foot end portion of the respective hollow table side frame members 192. As viewed in FIG. 4, outside walls of the table side frame members 192 are formed with an elongated slot 192*a* along the center of finite length and each support leg 228 is provided with an outwardly projecting stop pin 230 disposed to slide in a slot 192*a* and limit the relative telescopic movement of the support legs 228 in the side frame members.

Figure 20:
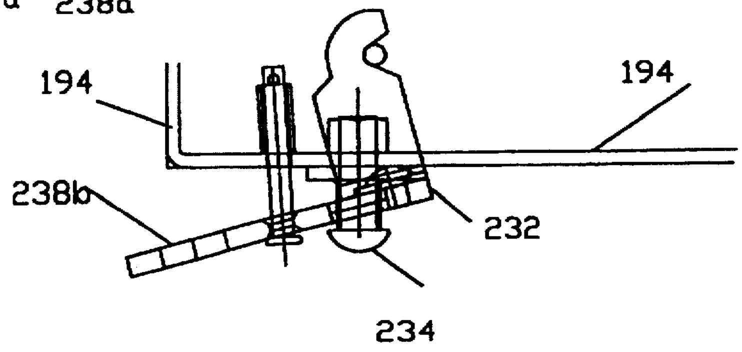
FIG. 20 is a fragmentary, side elevational view of a latch plate assembly of the foot board control and latch mechanism shown in an unlatched position.

In order to control the position of the foot board 106 relative to the table 102 and to latch the foot board in place once the desired position is attained, there is provided a latch plate 232 supported from the table cross-member 194 on a pair of pins 234 and biased upwardly by return springs 236 (FIG. 20). The latch plate 232 is formed with a pair of outwardly projecting ears 232*a* at opposite ends (FIG. 19), each ear having a rectangular-shaped aperture 232*b* therein dimensioned to receive a depending tooth 238*a* of a plurality thereof formed along a lower edge of a ratchet bar 238 secured to the outside of the adjacent support leg 228 by a pin 240 at the outer end and a stop pin 230 at the opposite end. The pins 230 are mounted on the support legs 228 and extend out through the slots 192*a* in the tubes 192, thus allowing the ratchet bars 238 to move in unison with the foot board 106 and the support legs 228 and may be latched into engagement with a particular tooth 238*a* seated in the opening 232*b* of the latch plate 232 in a latched position.

Figure 18:
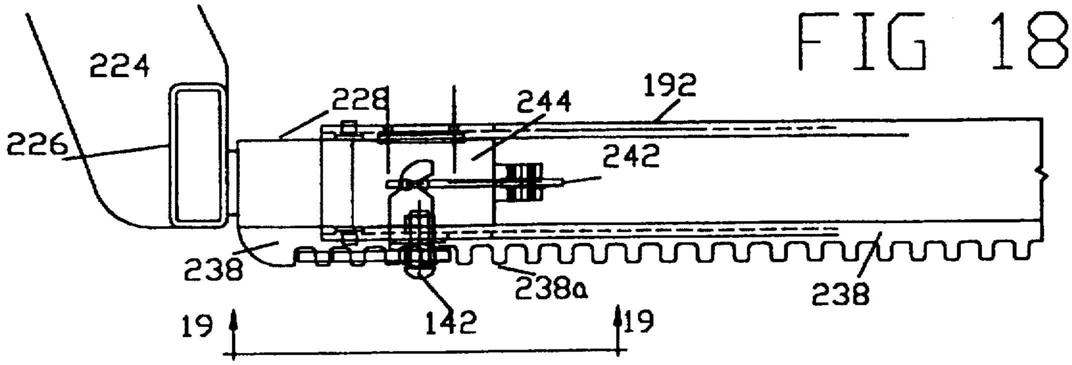
FIG. 18 is an enlarged fragmentary side elevational view of a foot board control and latch mechanism of the apparatus.

In order to latch and unlatch the latch plate 232 into and out of latch engagement with the ratchet bars 238, a U-shaped push bar 242 controlled by a latch solenoid 244 is energized and deenergized to release and hold the latch plate in a latching position (FIG. 18) and an unlatched position (FIG. 20) so that the foot board 106 may move outwardly from the foot end of the table 102 for mounting and dismounting of a patient 104 while the table is in the upright 70° tilt position and for adjustment of the foot board position (FIGS. 11A, 11B, 11C) away from the knee support cushion 110. The ratchet bars 238 have upwardly projecting triangular-shaped portions 238*b* providing support for the ankle cushion 108 attached thereto with fasteners 246 (FIG. 10).

Figures 21A, 21B, 22A, 22B:
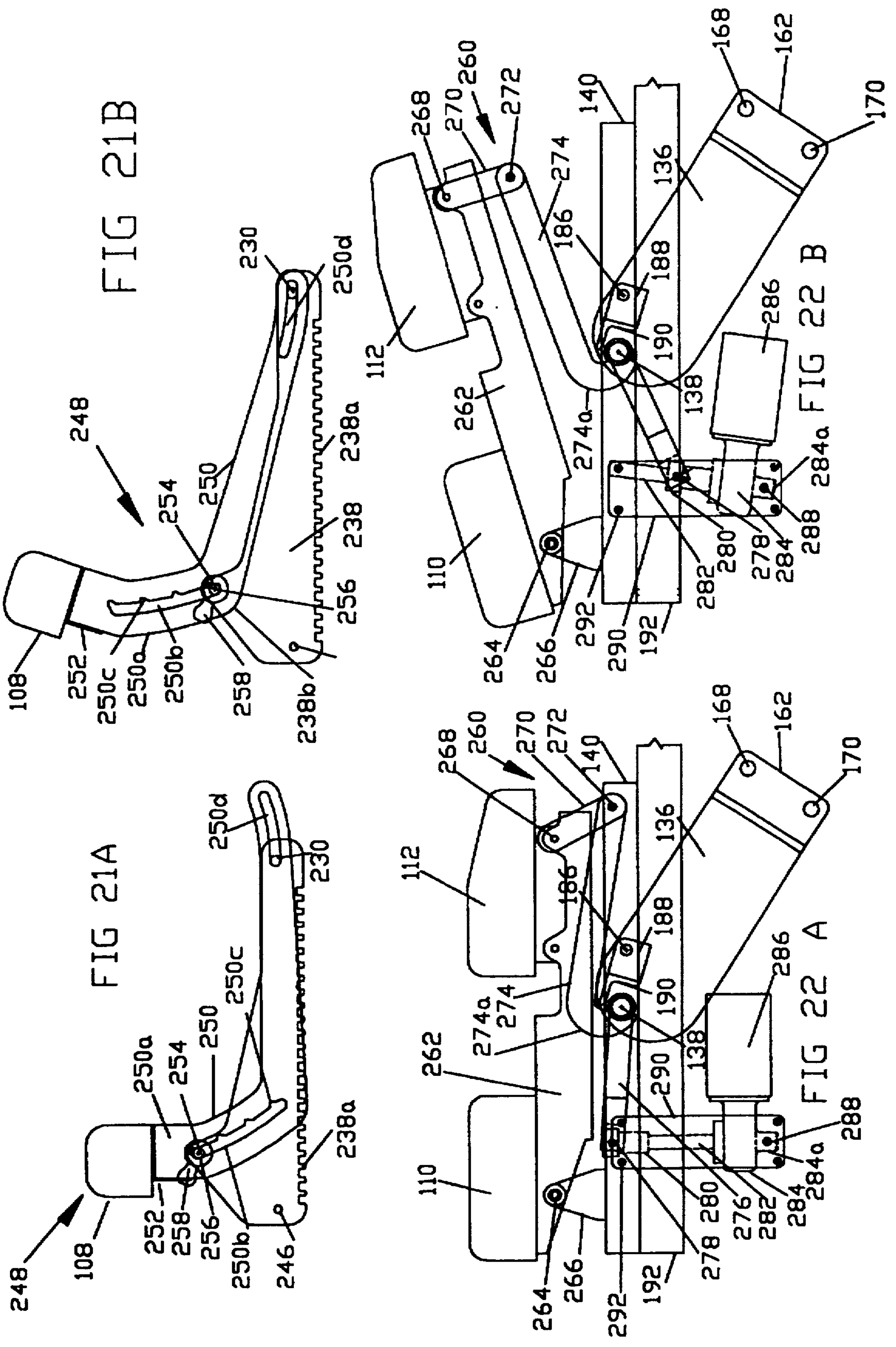
FIGS. 21A and 21B are side elevational views of an ankle rest support system of the apparatus shown in different operational positions.
FIGS. 22A and 22B are fragmentary side elevational views of a pelvic cushion tilt system for the apparatus shown in several different operational positions.

Referring now to FIGS. 21A and 21B, the apparatus 100 may be equipped with a height and distance adjustable support system 248 for supporting the ankle cushion 108 at different heights and slightly different distances away from the knee cushion 110. In the system 248, a pair of generally L-shaped side supports 250 are mounted on the ratchet bars 238 for relative movement thereon between several alternate positions of height and spacing distance relative to the table 102 and the knee cushion 110. Upper ends of upwardly projecting foot end portions 250*a* of the side supports 250 are interconnected with an angle cross-member 252 on which the ankle rest cushion 108 is mounted. The foot end portions 240*a* are formed with an elongated slot 250*b* having a plurality of notches 250*c* at different levels therein for receiving a radial latching lug 254 extending outwardly from a latch shaft 256 extending through the slot 250*b* and an upper end portion of the triangular portion 238*b* of a ratchet bar.

The latch shaft 256 is provided with radially outwardly extending latch knobs 258 at opposite ends for rotating the shaft between a latched position (FIG. 22A and 22B) wherein the latch lugs 254 are seated within notches 250*c* at a selected height level in the slots 250*b* and an unlatched position wherein the lugs are generally aligned with the slots 250*c* permitting free height adjustment between a maximum level (FIG. 21B) and a minimum level (FIG. 21A) and several intermediate level positions. At a head end portion of the L-shaped side supports 250, there is provided an elongated central slot 250*d* in which is seated the stop pin 230 which projects outwardly through the elongated slots 192*a* in the side frame members 192 from the support legs 228 to support the ratchet bars 238 and the L-shaped side supports 250 on each side of the table frame.

Referring now to FIG. 22, therein is illustrated a pelvic tilt and control system 260 for supporting the knee cushion 110 and pelvic cushion 112 in a horizontal treatment position (FIGS. 6, 7 and 8) and a tilted position (FIG. 9) up to 15° or more above the horizontal position for patients 104 that are pregnant or have special problems such as enlarged stomachs or abdomens. The pelvic tilt system 260 is adjustable and pre-programmable for a particular patient 104 and can provide sloping elevated support for the patient's knees 104*g* and thighs at an infinitely variable slope angle from the horizontal up to a maximum elevation at the head end or upper end of the pelvic cushion 112.

The cushions 110 and 112 are supported from a pelvic sub-frame 262 which is pivotally mounted adjacent a lower or foot end portion on a pelvic tilt axle or pin 264 carried on a pair of support brackets 266 mounted on the side members 140 of the table 102.

The upper or head end of the pelvic sub-frame 262 is pivotally secured by pins 268 to a pair of upstanding links 270 having lower ends pivotally connected via pins 272 to a head end portion of a pelvic tilt-link 274 having a downwardly curved lower or foot end portion 274*a* secured to the table tilt pin 138 so that the tilt-link will pivot about the axis of the table tilt pin between a lowermost position shown in dotted lines in FIG. 22A and an uppermost tilted position shown in FIG. 22B. The amount of angular rotation of the tilt-link 274 about the table tilt pin 138 is controlled by a pair of actuator levers 276 having a head end secured to the curved portion 274*a* of the tilt-link 274 on the table tilt pin 138 and a lower or foot end portion secured by pins 278 on opposite sides of an internally threaded, annular drive collar 280.

The drive collar 280 is mounted for movement up and down on a pelvic tilt jack screw 282 projecting upwardly from a right angle gear reducer 284 driven by an electrically powered, reversible DC motor drive 286. The gear reducer 284 is provided with an ear 284*a* mounted on a support pin 288 extend transversely of the table frame members 192 and supported by one or more dependent brackets 290 attached to the side frame members 140 with fasteners 292.

When the pelvic tilt drive motor 286 is energized to rotate the jack screw 282 in one direction the drive collar 280 is moved downwardly on the jack screw causing the tilt-links 274 to pivot in a counterclockwise direction to raise the angle of tilt of the knee cushion 110 and pelvic cushion 112 relative to the horizontal. When the pelvic tilt motor 286 is energized to rotate in an opposite direction, the jack screw collar 280 moves upwardly on the screw 282 causing the tilt links 274 to rotate in a clockwise direction to lower the cushions 110 and 112 back toward a horizontal position.

Referring now specifically to FIGS. 23A, 23B, 24 and 25, the apparatus 100 includes a front section 294 providing support for the abdominal cushion 114, breast cushion 116, the arm rests 118L and 118R and the head piece 120, which head piece may be of a type similar to that shown in U.S. Pat. No. 5,192,306 incorporated herein by reference.

The cushions 114 and 116 are supported on a base structure 296 pivotally supported at a head end on a transverse pivot axle or pin 298, in turn supported on a pair of upstanding side brackets 300 mounted at the forward end of a slide frame 302 which includes an upstanding, transverse head piece mounting plate 304. The slide frame 302 includes a pair of guide rods 306 telescopingly mounted on pairs of longitudinally spaced apart bearing blocks 308 (FIG. 25) mounted internally of the elongated longitudinal hollow tubular side frame members 192 of the table 102.

Figure 25:
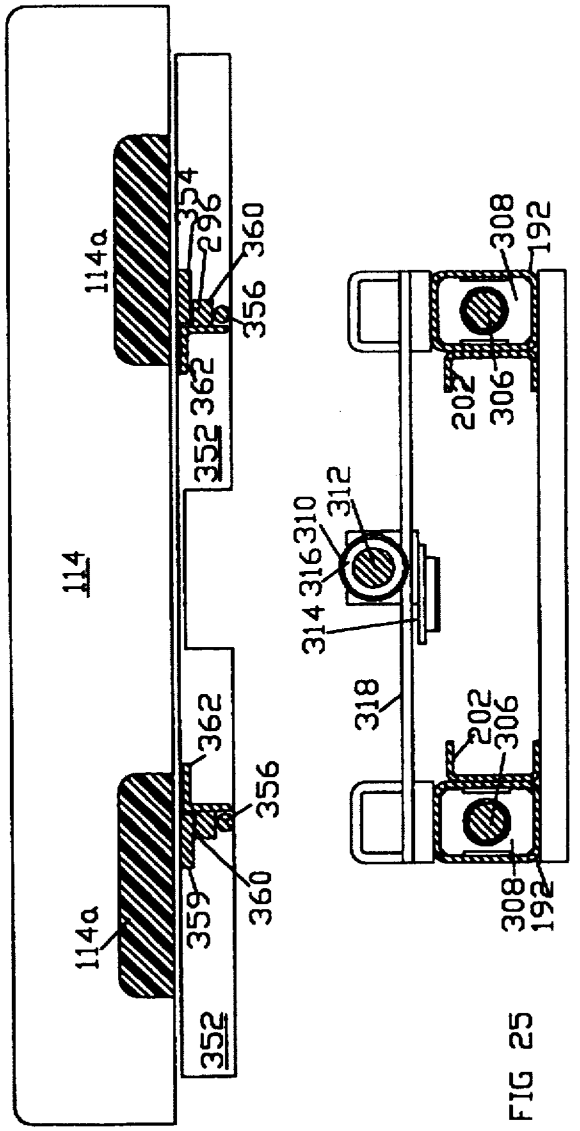
FIG. 25 is a transverse cross-sectional view taken substantially along lines 25—25 of FIG. 23A.

Longitudinal sliding movement of the front section 294 to accommodate a particular patient 104 is controlled by an electrically powered linear actuator 310 including a rotatable jack screw 312 which is powered by a front section reversible electrically powered DC motor and reduction gear box 314 similar to the other motors herein described. The jack screw 312 is threadedly engaged in an internally threaded sleeve 316 and mounted on a cross-bar 318 extending between and connected to the table side frames 192. Rotation of the jack screw 312 drives the internally threaded sleeve 316 mounted on the head piece mounting plate 304 connected to the guide rods 306 (FIG. 25). Rotation of the jack screw 312 in one direction causes the front section to move toward a farther out head end position to accommodate a tall patient 104 while rotational movement of the jack screw in an opposite direction pulls the front section toward a retracted position (FIG. 11A) for a short patient. Again, the motor 314 is operatively controlled or pre-programmed to accommodate a particular individual patient 104 for mounting, dismounting and treatment as previously described in connection with FIGS. 3 and 4.

The foot end of the base 296 is provided with a pair of downwardly depending support legs 320, each having a laterally extending latch pin 322 at the lower end for securing, the base 296 in a fixed position. When the latch pins 322 are disengaged from a latched condition, the base 296, the abdominal cushion 114 and breast cushion 116 supported thereon are free floating to move upward from the horizontal position of FIG. 23A to an elevated tilting position up to about 15° above horizontal or a downwardly tilting position (FIG. 23B) down to about 15° below the horizontal. In the free floating mode, the foot end portion of the base 296 is biased upwardly by a coil spring 324 (FIG. 23A) connected at an upper end to an extension bar 326 at the head end of the base and at the lower end to a hook 328 on the head piece support plate. This upward bias is offset by the weight of a patient 104 lying on the front section 294.

In order to lock or latch the base 296 of the front section 294 in a selected position, either horizontal (FIG. 23A) or an upwardly or downwardly tilted position (FIG. 23B), the pins 322 are engaged in a selected one of a plurality of vertically spaced apart slots 330 defined between pairs of teeth and opening outwardly toward the rear or foot end of the table 102. The teeth are formed along an edge portion of a pair of arcuately-shaped ladders 332. The ladders 332 are supported at upper and lower ends on pivot pins **332*a* and are rotatable outwardly (FIG. 24) to become disengaged from the pins 322 by means of ladder pivot bar 334, each having an elongated slot 336 at the foot end for receiving a pin 338 at the inner end of a control shaft 340 having a control knob 342 at the outer end. When the pins 322 are out of engagement with the slots 330 in the ladders 332, the base 296 is free to pivot downwardly about the axis of the pins 298 at the head end of the base. In this mode, the base 296 is biased in a clockwise direction (FIG. 23A) about the axis of the pins 298**.

In order to raise the abdominal cushion 114 and breast cushion 116 on the base 296 to an upwardly tilted position above the horizontal (FIG. 23B) a knob 342 on either side of the table 102 is rotated in a counterclockwise direction, causing a latch arm 344 to rotate and become disengaged from a pin 322 permitting the base 296 to pivot toward an upwardly tilted position away from the horizontal in a clockwise direction about the head end pins 298. The ladder pivot bar 334 on one side of the table 102 is interconnected via linkage 346 to the ladder pivot bar on the other side of the table so that either shaft 340 and knob 342 can be used to activate a latch arm 344 as described.

In order to return the base 296 to a horizontal position from an upwardly or downwardly tilted position (FIG. 23B) the base is pushed downward at the foot end portion until the pins 322 engage and pass the latch arms 344 which are biased in a counterclockwise direction by latch coil springs 348. After the pins 322 pass the latch arms 344, the springs 348 return the arms to the home position (FIG. 23A) restricting pins from moving upwardly beyond the horizontal. The base 296 can be latched or locked in any position between a maximum upward tilt and a maximum downward tilt by pushing a knob 342 inwardly toward the center of the table with the pins 322 lined up with a particular slot 330 in a respective ladder 334. The pins 322 travel up and down with the base 296 along an arcuate path defined by a closed end, arcuate slot **350*a* (FIG. 23B) provided in a restraining plate 350. Ends of the slots 350*a* define the upper and lower limits of tilt of the base 296** away from the horizontal.

Referring to FIGS. 11A, 11B, 11C, 24 and 25, the abdominal cushion 114 has a pair of relatively thinner cushion sections **114*a* of generally triangular shape on opposite sides forming recesses for the breasts of female patients 104 lying on the table to provide comfort. The abdominal cushion 114 and the breast cushion 116 are shaped to closely interfit (FIG. 11A) for short patients and to move longitudinally apart relative to one another for taller patients (FIGS. 11B and 11C) on the support base 296. The breast cushion 116 is formed with an indented neck section 116*a* on the head end which is reduced thickness to accommodate the neck of a patient 104**.

Referring also to FIG. 25, the cushions 114 as well as all the other cushions 108, 110, 112, 116 and the cushion on the head piece 120 are formed of small cell, resilient foam material such as polyurethane or equivalent. The foam material has an integrally formed impervious outer skin which is easily cleaned and sanitized.

The foot end portion of the base 296 is provided with a cross-member 352 for supporting the foot end portion of the cushion 114 and the legs 320 which extend downwardly therefrom at opposite ends. A pair of flat bars 354 project toward the head end of the front section 294 on the underside of the base 296 and spaced below each bar there is provided a rod 356 forming a slot 358 for slide bars 360 which project outwardly from angular side supports 362 (FIG. 25) on the underside of the breast cushion 116. As viewed in FIGS. 23A and 23B, the slots 358 are longer than the longitudinal spacing between the slide bar 360 on each side angle support 362 under the breast cushion 116 so that the position of the breast cushion longitudinally with respect to the abdominal cushion 114 may be adjusted to accommodate a particular patient 104.

It is thus seen that the front section 294 as a whole, is movable longitudinally with respect to the head end of the table 102 so that spacing between the abdominal cushion 114 and the breast or thoracic cushion 116 can be adjusted. In addition, the longitudinal spacing between the abdominal cushion 114 and the breast cushion 116 can be adjusted as desired. Moreover, the abdominal and breast cushions 114 and 116 can be released to float pivot up and down around the pins 298 at the head end of the base 296 and the weight of the patient 104 on the front section is opposed by the spring 324. On the other hand, the abdominal and breast cushions 114 and 116 can be latched or locked into a fixed position ranging from the horizontal (FIG. 23A) to upwardly and downwardly tilted positions (FIG. 23B) as previously described between maximum angular limits.

Figures 11A, 11B, 11C:
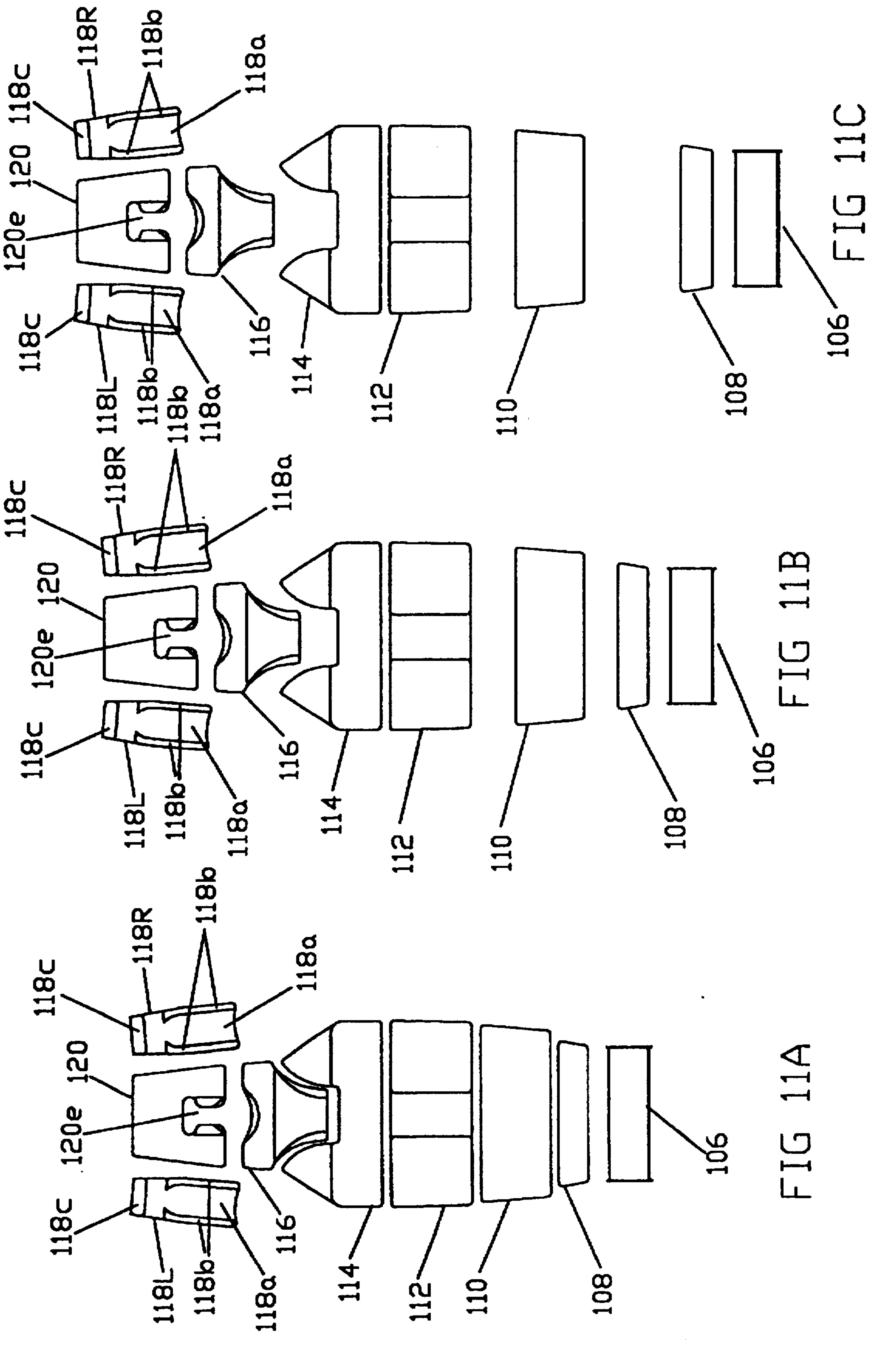
FIGS. 11A, 11B and 11C are schematic top plan views of the patient support cushions of the apparatus shown in several different positions for accommodating patients of different size and shape.

The arm rests 118L and 118R on opposite sides of the head support or head piece 120 are attached at the foot end to a cross-bar 364 secured to the lower end of the head piece mounting plate 304 at the head end of the front section 294. It should be noted that an upper surface of each arm rest 118L and 118R includes an elongated, central flat portion **118*a*, flanked on opposite sides with upstanding side walls 118*b*, and has indented transversely extending portions 118*d* for a patient's hands. Each arm rest 118L and 118R has a rounded outer free end portion 118*c* for gripping by the patient 104 when desired, especially during mounting, dismounting and table tilting and height moving operations as described. Also, as best shown in FIGS. 11A, 11B and 11C, each arm rest 118L and 118R is formed with the upstanding side walls 118*b* on opposite sides of the flat central portion 118*a* to provide a channel accommodate the forearm of a patient 104**.

Figure 23A:
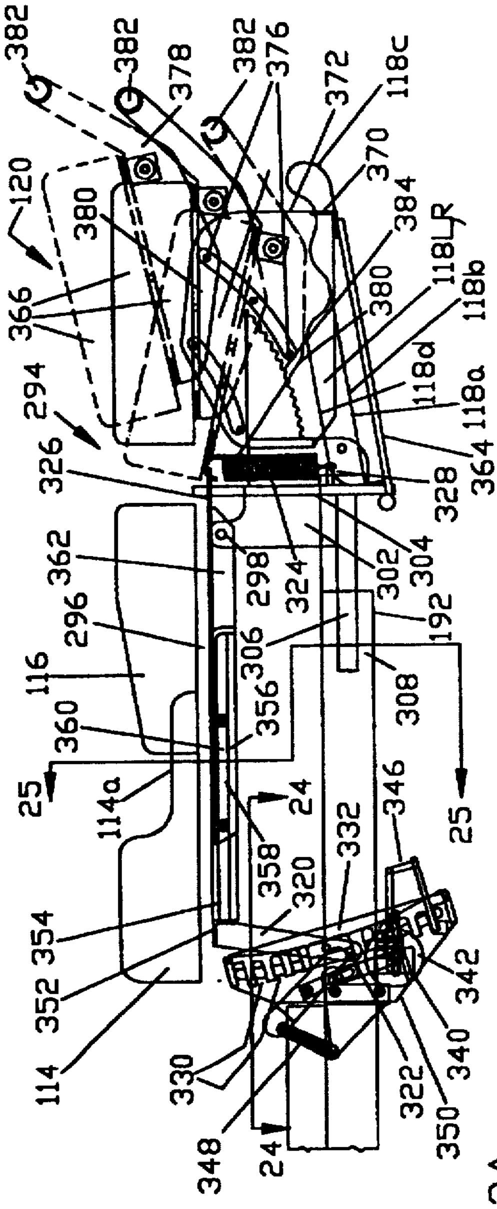
FIG. 23A is a side elevational view of a front section of the apparatus illustrating the abdominal and breast cushions and the head piece in several alternative positions.
Figure 23B:
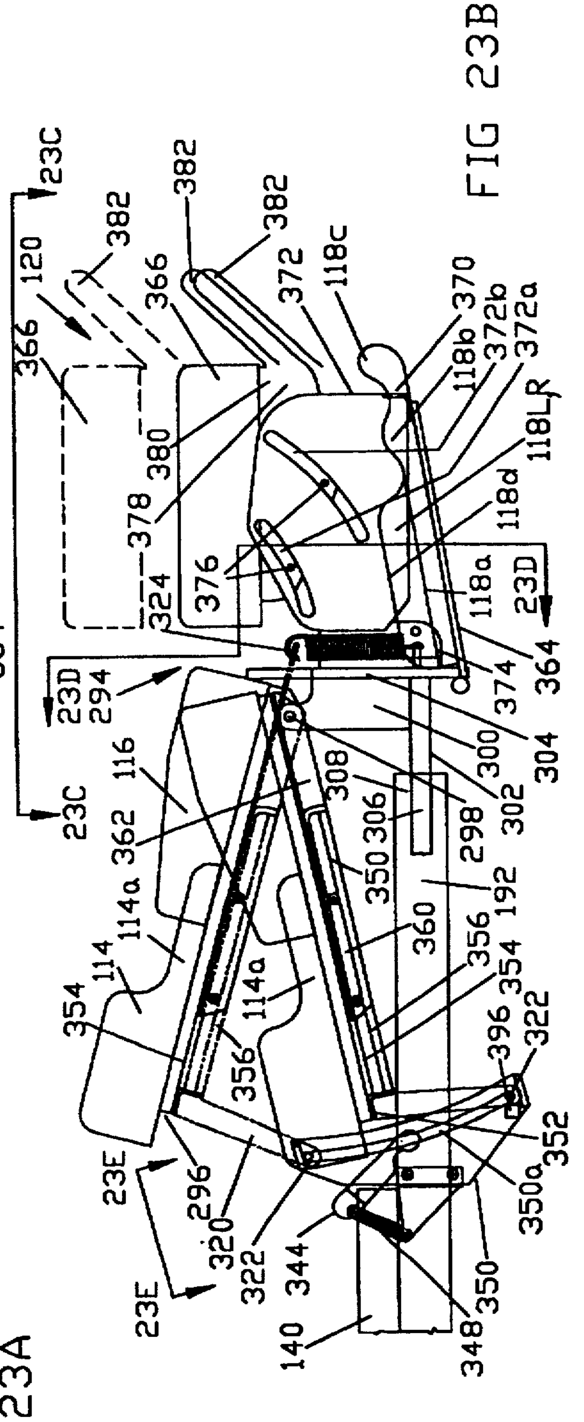
FIG. 23B is a side elevational view of the front section illustrating the abdominal and breast cushions in an alternate position and the head piece in several alternate positions.
Figure 23E:
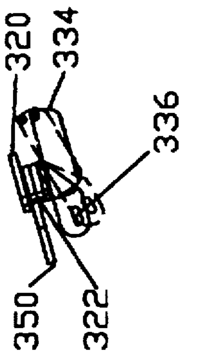
FIG. 23E is a fragmentary plan view taken substantially along lines 23E—23E of FIG. 23B.

Referring again to FIGS. 23A, 23B and 11A, 11B and 11C, the head piece 120 includes a head supporting cushion 366 having an upper surface which can be aligned even with the upper surface of the breast cushion 116 in a horizontal position (FIG. 23B) or can be elevated above the normal breast cushion level as much as 4½" inches or dropped below the level as much as one inch. In addition, the upper surface of the head cushion 366 can be tilted up or down at an angular position relative to the horizontal (FIG. 23A).

Figure 23D:
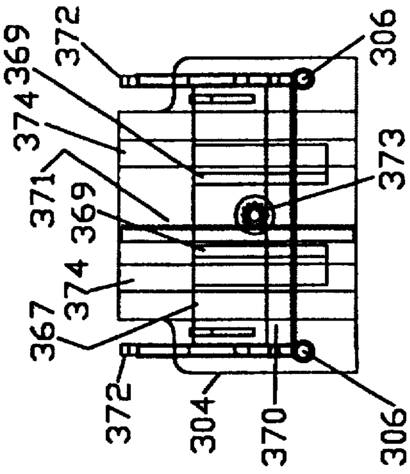
FIG. 23D is a vertical cross-sectional view taken substantially along lines 23D—23D of FIG. 23B.
Figure 23C:
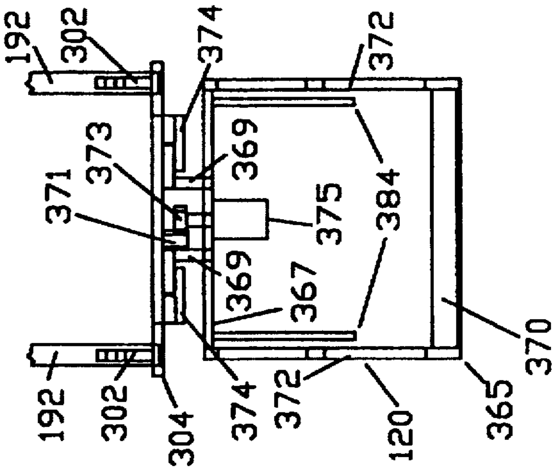
FIG. 23C is a horizontal cross-sectional view taken substantially along lines 23C—23C of FIG. 23B.
Figure 24:
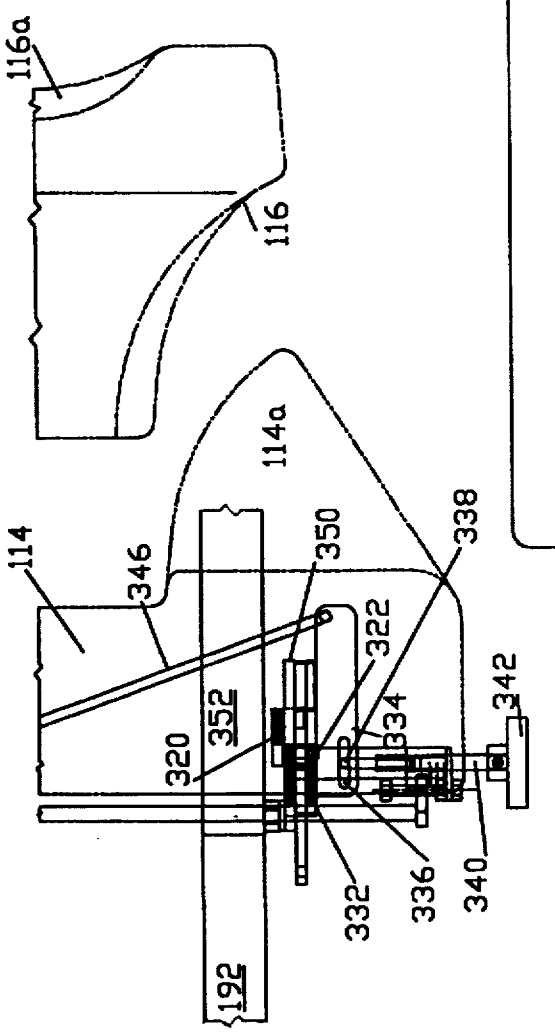
FIG. 24 is an enlarged, fragmentary, horizontal cross-sectional view taken substantially along lines 24—24 of FIG. 23A.

Referring to FIGS. 23C and 23D, the head piece 120 includes a frame 365 having a vertical inner end plate 367 on which are mounted a pair of laterally spaced apart vertical guide rails 369 of angular transverse cross-section. These angular guide rails 369 are slidably disposed in vertical guide members 374 on the support plate 304 to permit raising and lowering of the head piece 120 relative to the front section cushions 114 and 116. Movement of the head piece 120 to selected levels along the guide members 374 is controlled by a toothed rack 371 and pinion gear 373 mounted on the base plate 304 and inner end plate 367 of the head piece respectively. The pinion gear 373 is driven to rotate by a reversible electric motor 375 mounted on the head piece frame 365 and the motor is controlled by a 3-way switch 377 having UP, DOWN and OFF positions for selectively energizing the motor to raise and lower the head piece as desired.

The side plates 372 of the head piece 120 are supportively connected at the inner ends to vertical guide members 374 mounted on the outer surface of the head piece support plate 304. Each side support plate 372 is formed with an arcuately curved upper slot **372*a* and an arcuately curved lower slot 372*b* for slidably receiving pins 376 extending outwardly from opposite sides 378 of an undercarriage 380 below the head piece cushion 366. The undercarriage 380 is provided with an outwardly extending handle 382** for making tilt and level adjustments for the head piece cushion as shown graphically in FIGS. 23A and 23B.

As previously indicated, the head piece 120 may be of the type shown and described in U.S. Pat. Nos. 5,192,306 and/or 4,660,549, incorporated herein by reference, or may be of another less complex type without all of the features of the patented head pieces. In any event, the head piece 120 is mounted and supported to provide different heights or levels as desired and different angles of tilt as described, and a curved, toothed, ratchet plate 384 engaged by a handle controlled panel 386 is provided to latch the head piece in a desired position (not shown).

Figure 34:
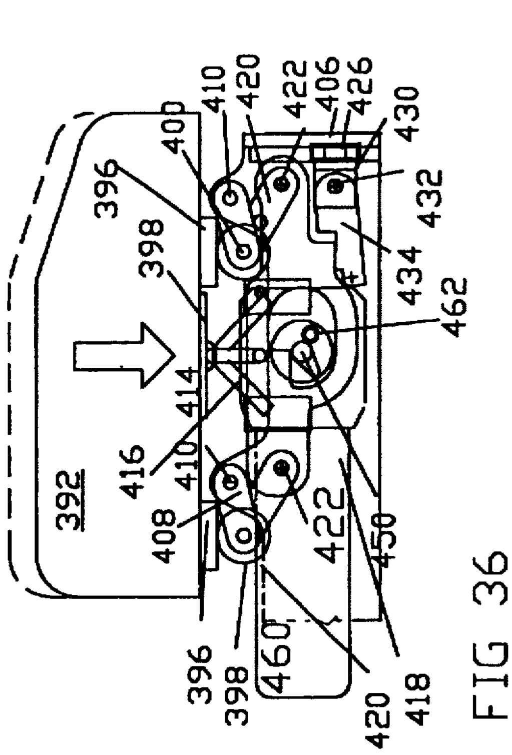
FIG. 34 is a diagrammatic side elevational view of the drop mechanism showing the drop mechanism after a vertical drop has been completed.

In accordance with an important feature of the present invention, one or more of the patient support cushions 112, 114, 116 and 366, may be supported on an automatic, electrically powered, self-cocking drop mechanism 390 shown in FIGS. 26–39 wherein the cushions are collectively given the reference number 392 and a supporting framework for the drop mechanism is given the reference number 394. As best shown in FIGS. 26, 27 and 37–39, the underside of the patient support cushion 392 is provided with a plurality of spaced apart roller support pads 396 located generally adjacent corner portions of the cushion and the pads rest on rollers 398 mounted at opposite ends of a pair of roller shafts 400 extending transversely to opposite side frame members 402 of the support framework 394 (FIG. 27) which includes parallel cross-members 404 and 406. Each shaft 400 is pivotally supported adjacent an outer end of link 408 and each link is pivotally attached at an opposite end to an upstanding ear on the upper edge of a side frame member 402 by a fixed pivot pin 410. As the links 408 pivot in a counterclockwise direction from an upper position (FIG. 33) toward a downward position (FIGS. 34–36) about the fixed mounting pins 410 on the side frame members 402, the cushion 392 drops vertically approximately one-half inch.

Figure 36:
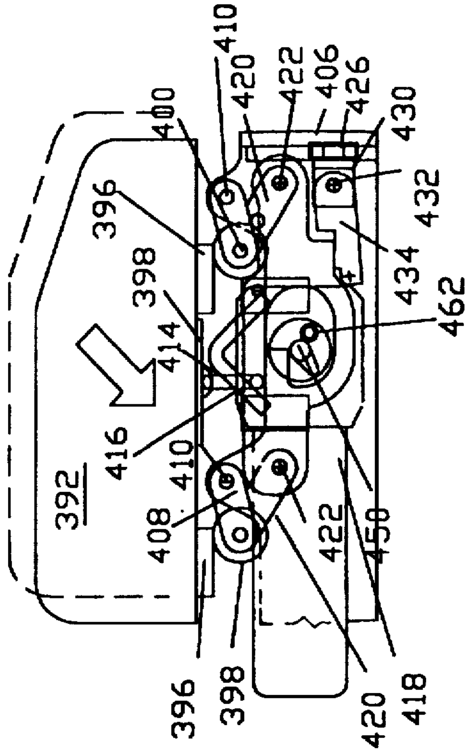
FIG. 36 is a diagrammatic side elevational view of the drop mechanism after a rearwardly sloping drop toward the patient's feet has been completed.
Figure 35:
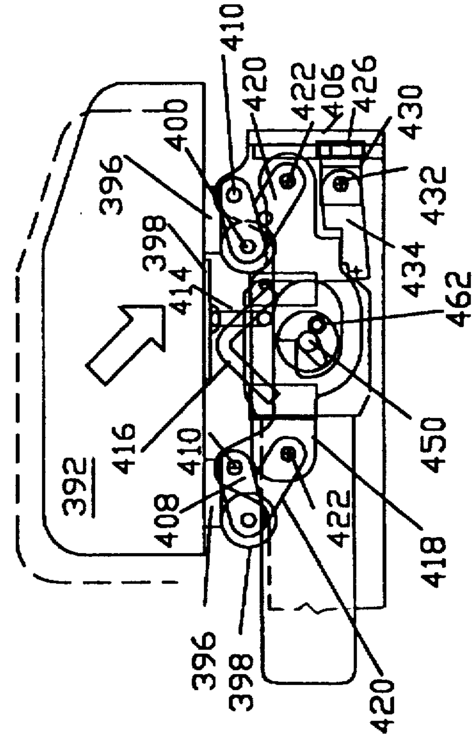
FIG. 35 is a diagrammatic side elevational view of the drop mechanism after a forwardly sloping drop toward the patient's head has been completed.
Figure 37:
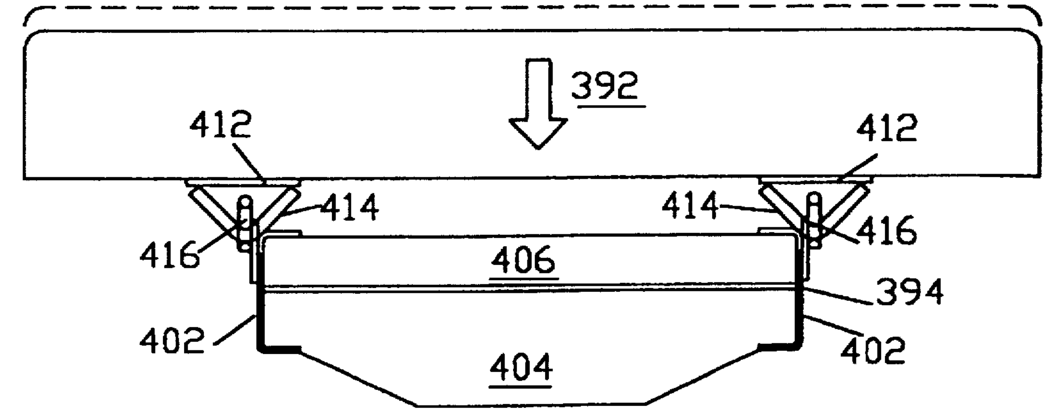
FIG. 37 is a diagrammatic transverse cross-sectional view of the drop mechanism taken substantially along lines 37—37 of FIG. 33 showing the drop mechanism after a vertical drop has been completed.
Figure 38:
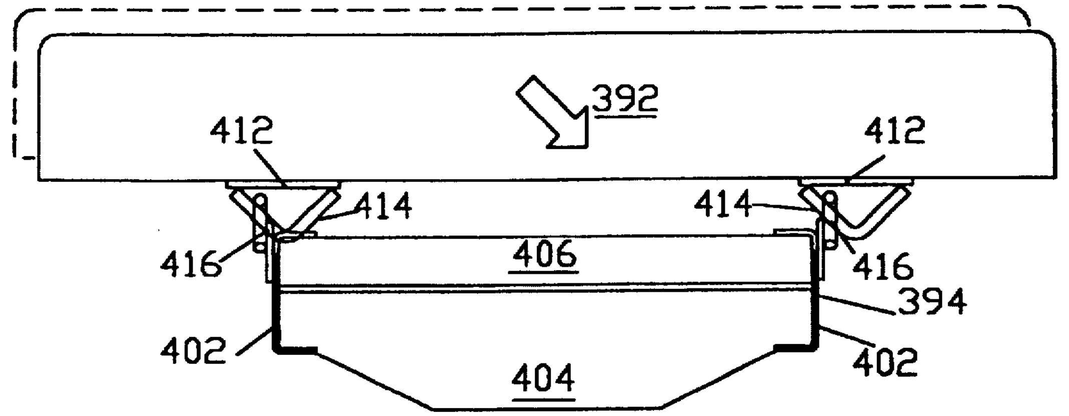
FIG. 38 is a diagrammatic transverse cross-sectional view of the drop mechanism after a laterally sloping drop toward a patient's side has been completed.
Figure 39:
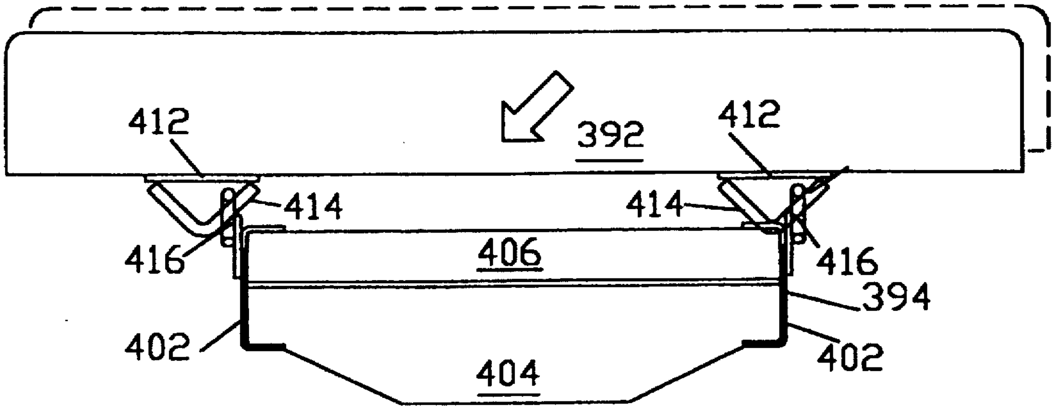
FIG. 39 is a diagrammatic transverse cross-sectional view of the drop mechanism after a laterally sloping drop toward a patient's opposite side has been completed.

In order to permit the cushion 392 to move down in a direction other than a straight vertical direction (FIGS. 35 and 37) and permit a practitioner to manually direct the cushion 392 to drop along a desired sloping or spiralling path both along a longitudinal axis of the table 102 as indicated by the large arrows in FIGS. 35 and 36 and along a transverse or laterally sloping path direction as indicated by the large arrows in FIGS. 38 and 39, the cushion is loosely interconnected to the framework 394 in a manner that limits the maximum amount of horizontal cushion shifting during a drop so that the pads 396 on the underside of the cushion do not move off of the respective supporting rollers 398.

The loose interconnection between the cushion 392 and the framework 394, includes a pair of square-shaped, upper connector pads 412 attached to the underside of the cushion adjacent opposite side edges as best shown in FIGS. 27 and 37–39. Each pad 412 supports a depending V-shaped, upper connector 414 aligned on a lateral axis parallel of and approximately midway between the cross-members 404 and 406 of the framework. These upper connectors are loosely interconnected with inverted V-shaped lower connectors 416 at right angles thereto attached to the upper edges of the side frames 402. If a chiropractor desires that a drop operation be directed at a thrust angle other than true vertical, the connector system as described will accommodate to permit a directional change of up to 45° away from true vertical in a longitudinal sense as well as a lateral sense and this feature provides exceptional drop treatment possibilities for a patient 104 and chiropractor utilizing drop therapy.

Figure 43:
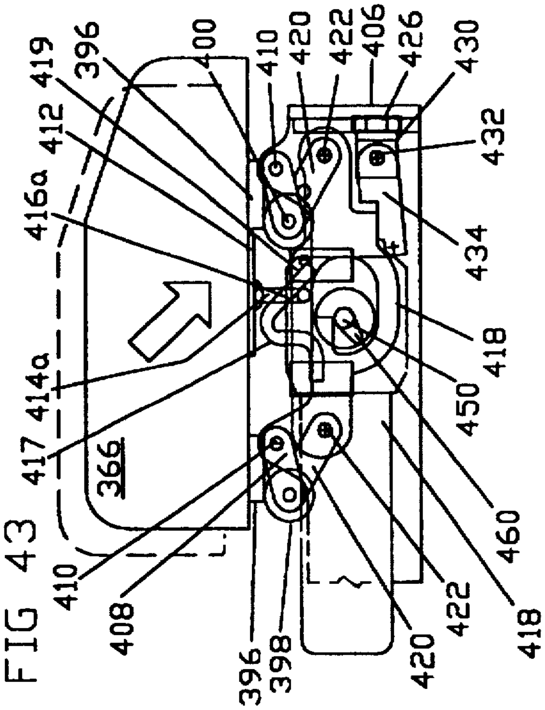
FIG. 43 is a side elevational view similar to FIG. 42 wherein a drop operation with a forward direction has been completed.
Figure 44:
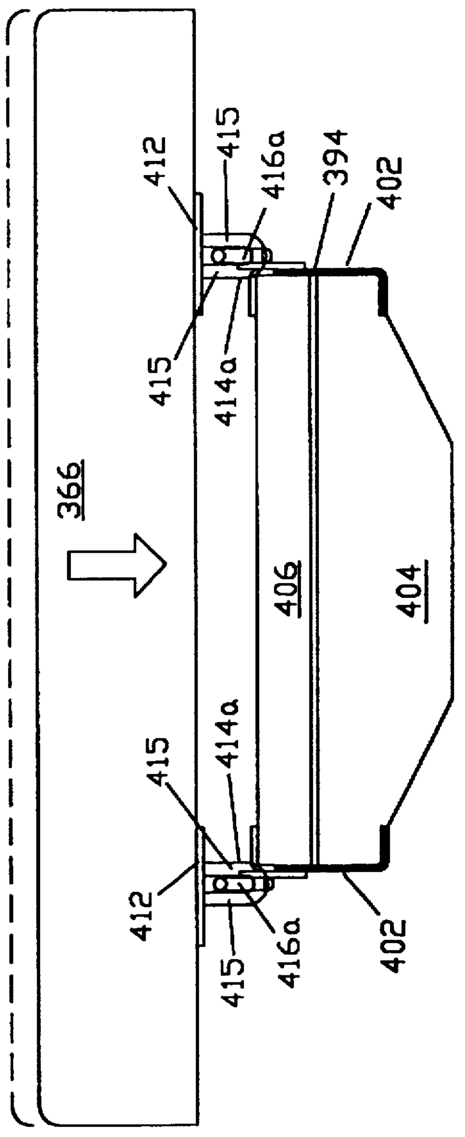
FIG. 44 is a transverse cross-sectional view taken substantially along lines 44—44 of FIG. 42.
Figure 42:
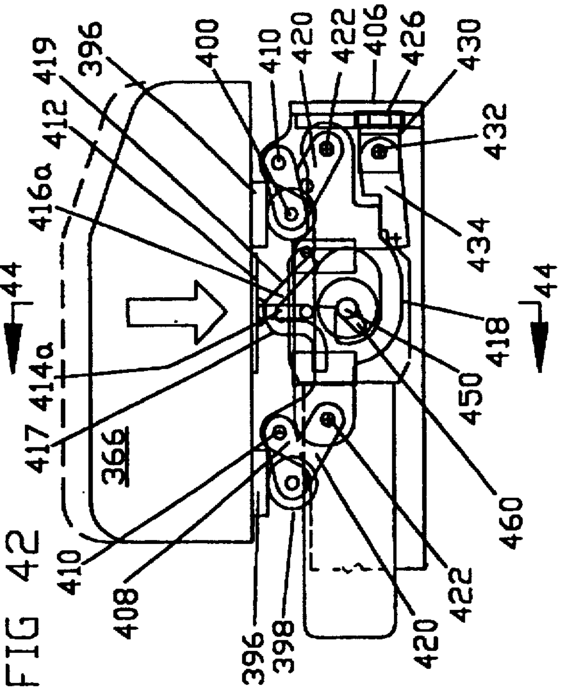
FIG. 42 is a side elevational view of a drop mechanism in accordance with the present invention for restricting a drop operation to a vertical or forward direction longitudinally and a vertical direction laterally.

Referring now to FIGS. 42, 43 and 44 therein is illustrated a modified connector system especially designed for the self-cocking drop mechanisms 390 used for treating the cervical area or other areas of a patient 104 wherein, as an example, it is desired to limit the direction of the drop to a forward or vertical direction only (FIGS. 43 and 42) without any lateral or side component. As illustrated, a pair of modified upper connectors 414A are secured to the pads 412 on the underside of the cushion 366 and these connectors are generally U-shaped in configuration with a pair of spaced apart parallel, vertical legs 415 extending in vertical planes on opposite sides of modified lower connectors 416A as best shown in FIG. 44. Any lateral force component inadvertently applied by a practitioner when initiating a drop is constrained to a true vertical in a lateral sense by the parallel opposite side legs 415 which are engaged in a sandwiched relation with modified lower connectors 416A at right angles to the upper connectors 414A.

The lower connectors 416A are designed to permit a straight down vertical drop (FIG. 42) and for this purpose have a vertical leg 417 on one side. On opposite sides a slanted or sloped leg 419 is provided (FIG. 43) permitting a forward slant or component to a drop. Both legs 417 and 419 of each connector 416A lie in a common plane generally parallel with the spinal axis of a patient 104 lying on the table 102. It should also be noted that various orientations and combinations of the loose connectors 414, 414A and 416 and 416A, respectively, can be used to restrict or confine the direction of horizontal movement to one or more planes relative to the patient 104 on the table 102 during drop treatments.

Figure 45:
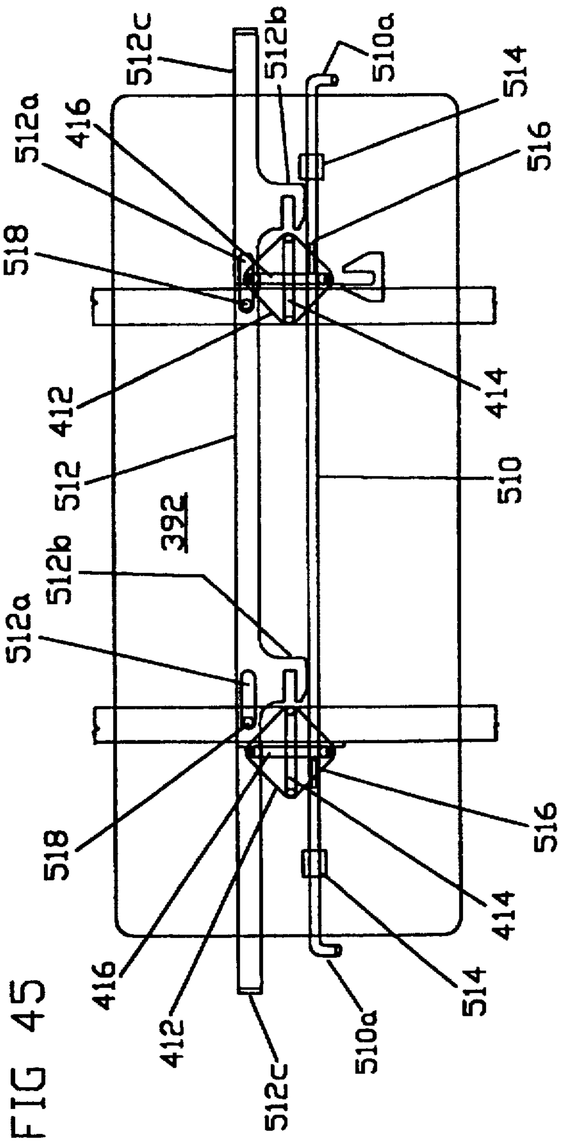
FIG. 45 is a bottom view of a universal selective lockout system for a drop mechanism in accordance with the present invention.
Figure 47:
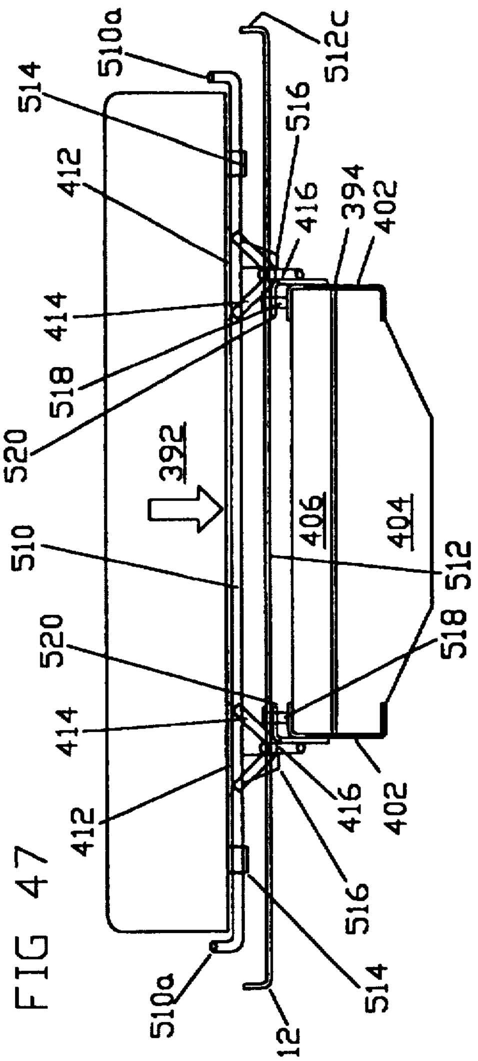
FIG. 47 is a transverse cross-sectional view taken substantially along lines 47—47 of FIG. 45.
Figure 46:
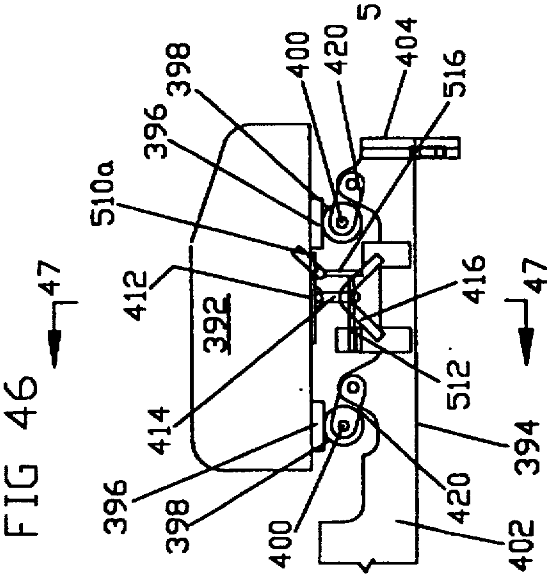
FIG. 46 is a side elevational view of the system of FIG. 45.

Referring now to FIGS. 45, 46 and 47, a further modified universal loose connector system may be utilized with the drop mechanisms 390 of the apparatus 100 wherein horizontal movement components during a drop can be selectively locked out in a longitudinal vertical plane, a lateral vertical plane or both planes when a pure vertical drop is desired. In the universal system, V-shaped upper loose connectors 414 and lower loose connectors 416 are utilized in combination with a lateral lockout control 510 and a longitudinal lockout control 512.

The lateral lockout control 510 includes an elongated rod having upturned handle segments 510*a* at opposite ends positioned outwardly on opposite sides of the support cushion 392 for easy access from both sides of the table 102. The elongated control rod 510 is supported for rotation about its longitudinal axis on a pair of pillow blocks 514 fixed mounted on the underside of the cushion 392. Attached to extend outwardly of the control rod 510 are a pair of stops 516 which may be extended vertically downwardly by rotation of the rod with either end handle 510*a* so that the stops are positioned to engage outside facing portions of the lower connectors 416 during a drop operation. The engagement between the stops 516 on the rod 510 and the lower loose connectors 416 prevents lateral horizontal movement of the cushion 492. Rotation of the rod handle 510*a* in a counterclockwise direction as indicated by the arrow in 46 to an unlocked position as shown in dotted lines moves the stops 516 out of position for contact with the lower connectors 416 so that lateral displacement of the cushion can take place during a drop operation.

The longitudinal lockout control 512 includes an elongated bar having slots 512*a* for receiving mounting pins 518 projecting upwardly from angle brackets 520 attached to the side members 402 of the support framework 394 (FIG. 47). The pin and slot connections between the control bar 512 and the pins 518 permit longitudinally sliding movement of the bar between an unlocked position (FIG. 45) and a locked position wherein slotted hook-like projections 512*b* are moved into position for engaging the upper loose connectors 414 which depend downwardly from pads 412 on the underside of the cushion 392. At each end the control 512 includes a short upturned handle segment 512*c* for facilitating movement of the longitudinal lockout control between locked and unlocked positions from either side of the cushion 392. When both controls 510 and 512 are moved to a locked position, a drop operation is restricted to a vertical direction only and when neither is locked the drop can move along a sloped straight or spiral path as directed by a practitioner.

In accordance with the invention, the automatic, self-cocking, omni-directional drop mechanism 290 includes an elongated drop link 418 which is pivotally interconnected at opposite end portions via bell cranks 420 and pins 422 to the shafts 400 which carry the rollers 398 supporting the cushion 392. When the drop link 418 is latched in a cocked position to the left as shown in FIGS. 26, 26A, 32 and 33, the cushion 392 is held at a maximum upper level ready for a drop operation to be initiated by a directionalized downward thrust applied to the patient 104 as illustrated by large arrows in FIGS. 34–39.

The exact value of the thrust force required to be exerted by a practitioner to initiate a drop may be selectively determined for each particular patient 104. The patient's actual weight that is supported on the cushion 392 is measured utilizing a force tranducer 426, such as a load cell or a strain gauge that is mounted on a bar 428 (FIG. 27) secured to the frame member 406.

Figure 33:
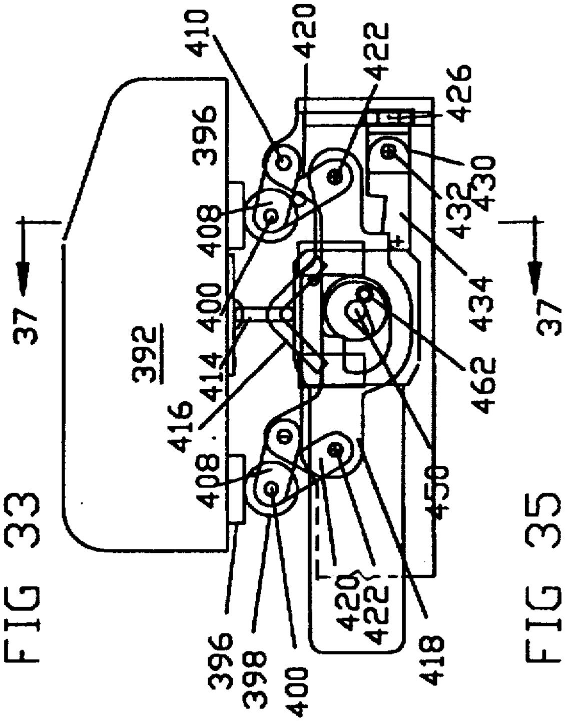
FIG. 33 is a diagrammatic side elevational view of the drop mechanism in a cocked position ready for a drop operation.

The strain gauge or load cell 426 includes a bracket 430 having a cross-pin 432 extending between spaced apart bracket legs and supporting an end portion of a latch 434. When the drop link 418 is cocked in an uppermost elevational position toward the left as shown in FIGS. 26A and 33, a notched out segment 434*a* at the upper left hand corner of the latch 434 is latchingly engaged with a vertical shoulder surface 418*a* on the lower edge of the drop link preventing rightward movement thereof. The latch 434 is biased in a clockwise direction to maintain latched engagement with the drop link 418 by a latch spring 436 having an upper end connected to a right hand bell crank 420 and a lower end connected to the latch by a bracket 438 and pin 440. A drop trip lever 442 is mounted on the pin 440 and projects upwardly thereof so that a narrow upper end portion 442*a* is engaged with a drop link pin 444 on the drop link 418.

Figure 28:
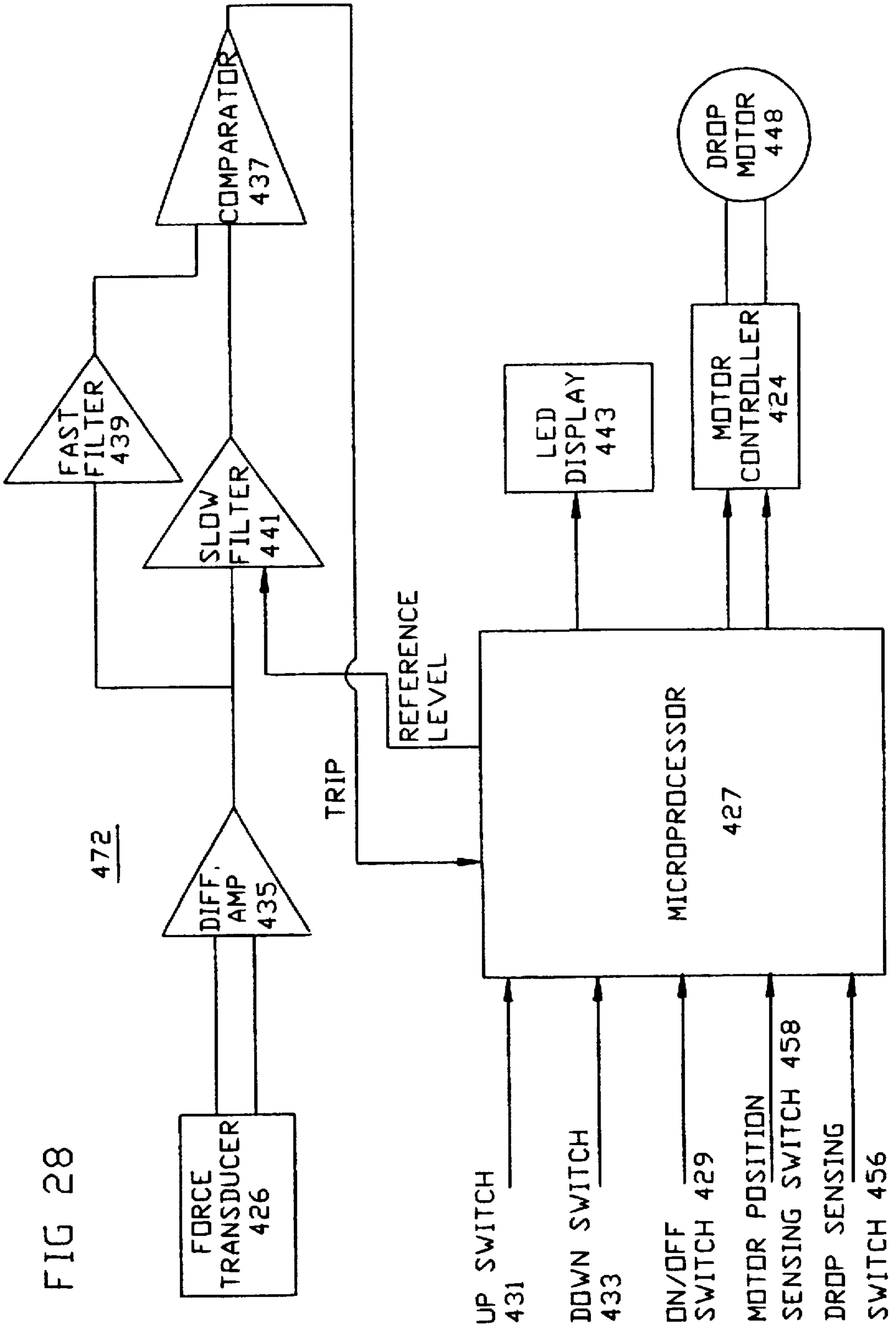
FIG. 28 is a schematic diagram of a drop control and drive system for the drop mechanism.
Figure 32:
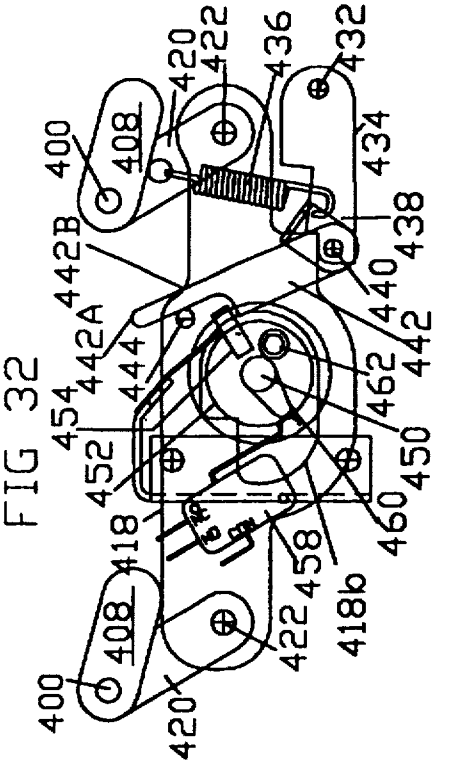
FIG. 32 is a diagrammatic side elevational view of the drop mechanism shown after automatic recocking has been completed and the drop mechanism is in a cocked position ready for the next drop operation.

Referring to FIG. 28, when a portion of a patient 104 is supported on the cushion 392, the added weight of the patient exerts a downward force on the rollers 398 and a counterclockwise bias on the bell cranks 420 connected to opposite ends of the drop link 418. This counterclockwise bias exerts a left to right thrust on the drop link 418 proportional to the weight of the patient 104 that is present on the cushion 392. In the upper or cocked position, the drop link 418 is restrained from movement from left to right because of the latching engagement between the drop link and the latch 434 (FIGS. 26A, 32 and 33). However, the force on the drop link 418 biasing the link toward the right is transmitted to the load cell 426 via the latch 434, pin 432, and bracket 430.

As shown in FIG. 28, a drop controller generally designated by the reference character 472 includes a microprocessor 427 that is suitably programmed for controlling the drop feature. Sequential steps performed by the microprocessor 427 are illustrated and described with respect to FIGS. 50A and 50B. A plurality of control switch inputs are applied to the microprocessor 427 for entering the practitioner's selections including an ON/OFF switch 429, an UP switch 431 and a DOWN switch 433. The ON/OFF switch 429 is operated by the practitioner to energize and enable the drop mechanism 390. The UP switch 431 and the DOWN switch 433 are selectively operated by the practitioner to select a threshold or sensitivity value of thrust force required to initiate a drop, as desired.

When the force as measured by the load cell or strain gauge 426 exceeds a value as preselected for a particular patient 104, a trip signal is applied to the microprocessor 427. The output signal of the force transducer 426 is applied to a differential amplifier 435 that removes common-mode noise from the output signal. The differential amplified output signal of the differential amplifier 435 is coupled to a comparator 437 via a fast filter 439 and a slow filter 441. A reference level at a line labeled REFERENCE LEVEL is applied to the filter 441 by the microprocessor 427 corresponding to the sensitivity level selected by the practitioner. Comparator 437 generates the trip signal applied to the microprocessor 427 at a line labeled TRIP. A light emitting diode (LED) display 443 operatively controlled by the microprocessor 427 displays the ON/OFF status of the drop mechanism 390, and displays the level of drop sensitivity. LED display 443 can be used to display a detected error condition for the drop mechanism 390.

Each drop apparatus 390 includes an electric, drop motor 448 that is operatively controlled by the microprocessor 427 via a motor controller 424. The drop motor 448 is energized to rotate a control shaft 450 (FIGS. 27, 29 and 30) via a through gear reducer 452. As the shaft 450 rotates clockwise from a cocked or latched position wherein the drop link 418 and the latch 434 are latchingly engaged (FIG. 26A) to an unlatched position of FIG. 29, a radial clutch pin 454 on the shaft and engaged with a shoulder surface 442*b* on the trip lever 442 causes the trip lever to move downwardly and bias the latch 434 in a counterclockwise direction against the spring 436 to release latching engagement between the latch and the drop link 418. When release of the latch 434 occurs, the drop link 418 is no longer restrained against movement toward the right and a drop operation occurs as the downward thrust on the patient 104 and cushion 392 becomes effective. As a drop occurs, the bell cranks 420 rotate in a counterclockwise direction from a high position (FIG. 29) to a low position (FIG. 30) and the cushion 392 rapidly drops about one-half inch either straight down (FIGS. 35 and 37) or on a straight slope or spiral path as directed by the thrust applied by a practitioner (FIGS. 34, 36, 38 and 39).

Clockwise rotation of the shaft 450 continues for a short time after the drop link 418 and latch 434 are unlatched until a drop sensing switch 456 is actuated (FIG. 31) by right hand movement of the drop link 418 and pin 422 away from the switch to stop electrical energization or deenergize the drop motor 448. The drop motor 448 is then energized to rotate the shaft 450 in a counterclockwise direction (FIG. 31) to begin automatic cocking action raising the cushion 392 back to the high or cocked position. A position sensing switch 458 is eventually actuated by a radial arm 460 on the shaft 450 to shut down the motor 448 when a fully elevated or cocked position is reached and the drop 390 is then ready for the next initiated drop operation (FIG. 32).

A roller 462 is positioned to move in a central opening **418*b* formed in the drop link 418 and the opening forming a cam surface having a horizontally elongated, generally elliptical shape with a tooth-like segment 463 at an upper left hand corner providing intersecting horizontal and vertical stop surfaces. The horizontal stop surface is positioned at a level above the shaft 450 permitting horizontal reciprocal movement of the drop link 418 relative to the shaft during a downward drop movement (drop link 418 moves to right) and an upward cocking movement (drop link 418 moves to left) of the cushion 392**.

Figure 30:
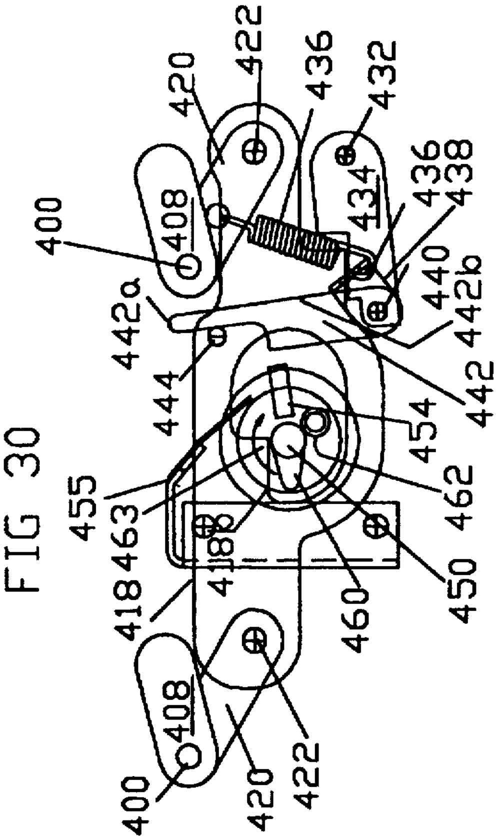
FIG. 30 is a diagrammatic side elevational view of the drop mechanism shown at the end of a drop operation.
Figure 29:
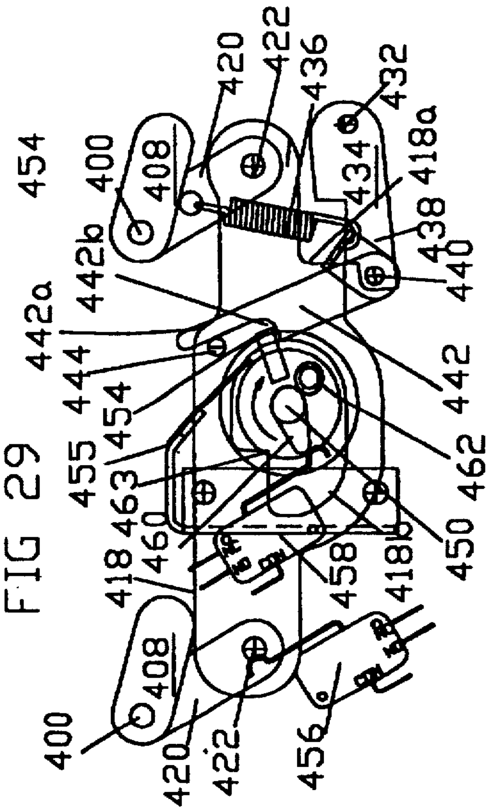
FIG. 29 is a diagrammatic side elevational view of the drop mechanism shown after unlatching has just occurred to initiate a drop.
Figure 31:
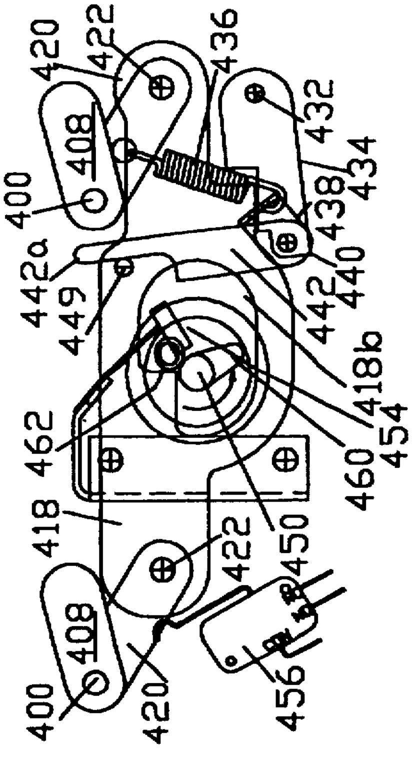
FIG. 31 is a diagrammatic side elevational view of the drop mechanism shown after an automatic recocking operation has commenced.

Referring to FIGS. 29 and 30, when a drop operation has been completed and the drop link 418 is in a right hand position, the motor 448 is stopped from further rotation in a clockwise direction opening of a drop sensing switch 456. Subsequently, upon rotation of the shaft 450 in a counterclockwise direction, a roller 462 mounted on an extension of the shaft 450 and located in the drop link opening **418*b* is moved upwardly in the opening on the right side of the shaft 450 until finally engaging the vertical stop surface of the tooth 463. This engagement causes the drop link 418 to move to the left (FIGS. 31 and 32) causing the cushion 392** to rise.

At the same time, the one way clutch pin 454 rotates counterclockwise until it contacts a stop 455. The clutch 454 then free wheels for the remainder of counterclockwise rotation of the shaft 450 during the recocking cycle. In this position, the spring 436 is free to elevate the latch 434 into latching engagement with the drop link 418 to hold the drop link in a left hand, latched position until the next drop is initiated. The roller 462 and the radial arm 460 move to the left side of the shaft 250 (FIG. 32) and the arm continues to rotate in a counterclockwise direction until engaging a control arm of the motor position switch 458, which engagement deactivates the motor 448 via operative control by microprocessor 427.

Elevation of the cushion 392 and the patient 104 resting thereon during the automatic drop cocking operation as described, essentially requires no work by the chiropractor and accordingly, a number of successive drop operations can be conducted on one or more patients without producing chiropractor fatigue. Moreover, the amount of force required to initiate a drop is precisely controlled and pre-programmed by the practitioner selective adjustment using up and down switches 431 and 433. In addition, the direction of the thrust applied to initiate a drop operation is adjustable as decided by the chiropractor.

The drop mechanism 390 requires only about 2½" in height between the base of the cushion 392 and a main supporting frame. The apparatus 100 can be assembled to include no drop mechanism 390, at least one or more drop mechanisms or a drop mechanism for all of the cushions 112, 114, 116 and the cushion 366 of the head piece 120. When some but not all of the cushions are provided with drop mechanisms 390, mounting brackets are provided for the cushions not having drop mechanisms associated therewith to correctly position the cushions relative to adjacent cushions.

Figure 40:
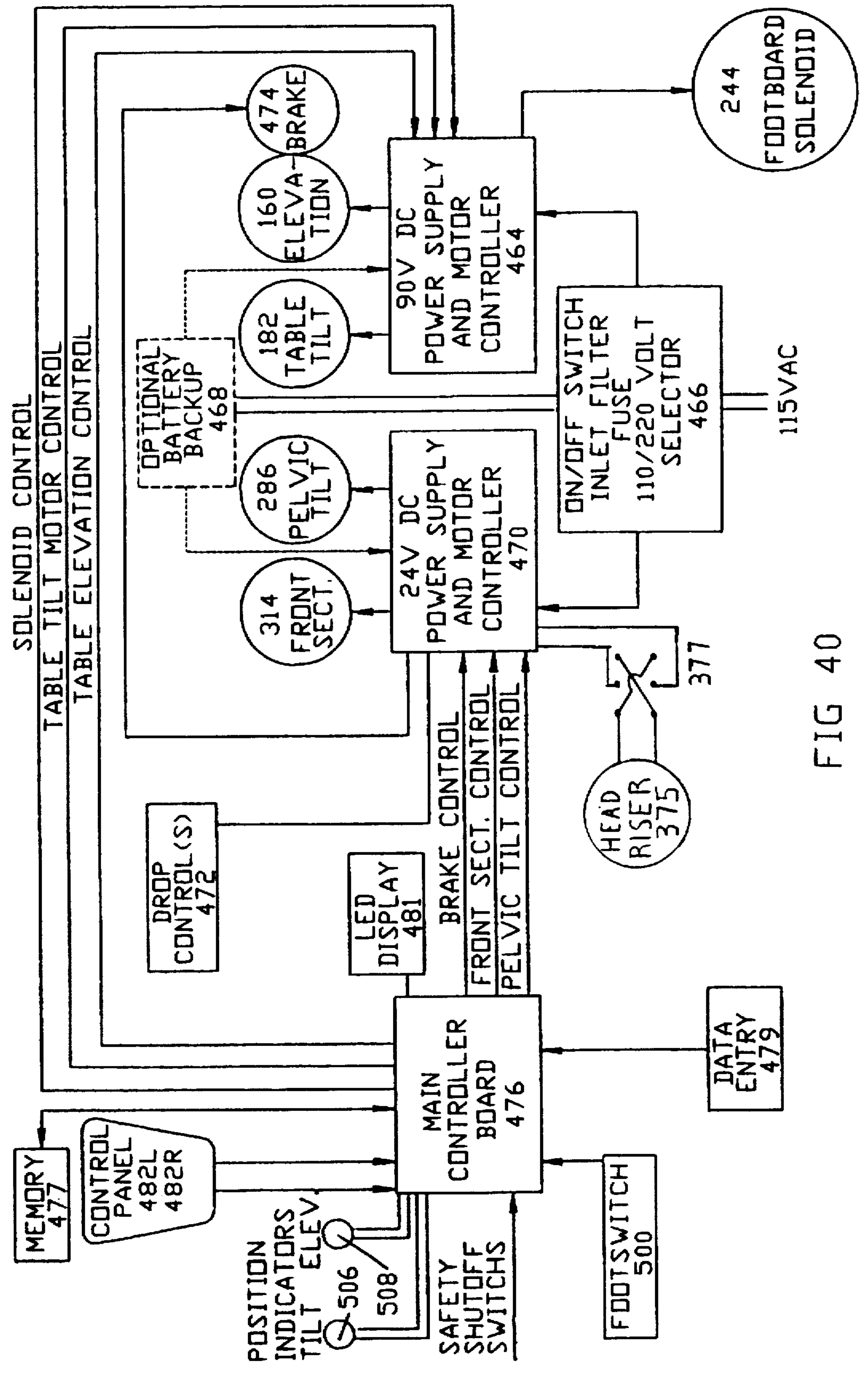
FIG. 40 is a schematic diagram of an electrical power and control system of the apparatus.
Figure 41L:
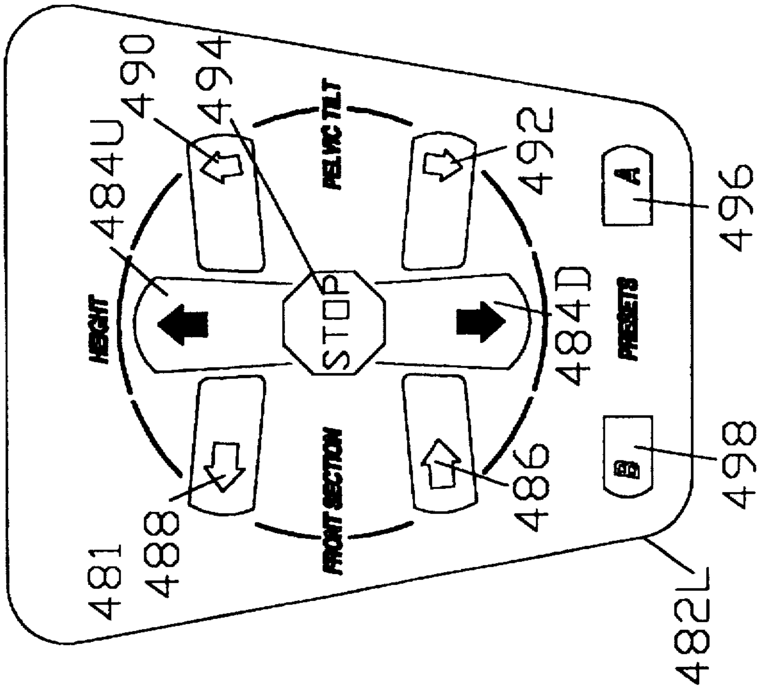
FIGS. 41L and 41R are elevational views of an elevation and tilt control panel for the apparatus.
Figure 41R:
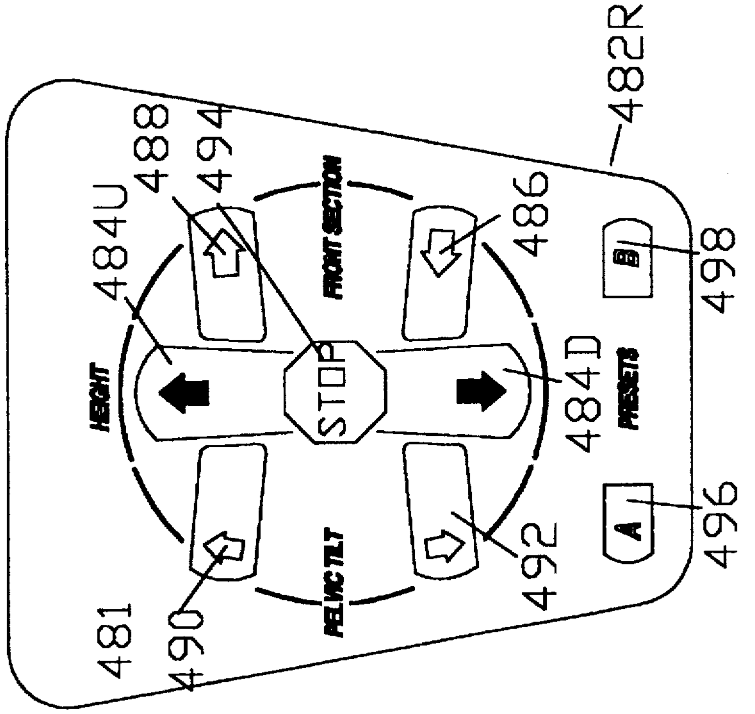

Referring now to FIGS. 40, 41L and 41R, the apparatus 100 is an all electrically powered unit requiring no hydraulics as do many prior art treatment tables. As shown in FIG. 40, the table tilt motor 182 and table elevation motor 160 are operatively controlled and supplied with 90V DC power from a power supply and motor controller 464 as is the foot board solenoid 244. Normally, the controller 464 is supplied from a primary, filtered AC power supply 466 energized from a convenience outlet or primary AC line power source. As an option, a battery back-up 468 may be provided for supplying electrical power to the controller 464. Power from the main AC power supply source 466 or the optional battery back-up power source 468 is also supplied to a 24V DC power supply and motor controller 470, which, in turn, provides electrical power for operating any drop mechanism 390 included on the apparatus 100 via the drop controller 472. The 24V controller 470 also provides power for an electrical brake 474 associated with the elevation stepping motor 160. The 24V DC controller operatively controls and provides electrical power for the front section motor 314 and the pelvic tilt motor 286.

The all-electrically powered apparatus 100 includes a main microprocessor or controller 476 and associated memory 477. Various commercially available devices can be used for microprocessor 476, such as an 8051 type device manufactured and sold by Intel Corp. of Santa Clara, Calif. Microprocessor 476 is operatively connected to the respective low voltage 24V DC controller 470 and the high voltage 90V DC controller 464, a plurality of control lines. The apparatus includes left and right side control panels 482L and 482R (FIGS. 41L and 41R) for use by a practitioner in controlling the height of the table up or down (buttons 484U and 484D), the amount of front section extension in or out (buttons 486 and 488), the amount of pelvic tilt up or down (buttons 490 and 492) and an octagonally-shaped center button 494 for emergency stopping of table movement.

The associated memory 477 can include a read only memory (ROM) for program storage and an electronically erasable programmable read only memory (EEPROM) for data storage. A data entry device 479 can be provided by a keyboard, bar code scanner or communications link such as to the practitioner's office computer, or combination of these devices. A LED display 481 is operatively controlled by microprocessor 476 for displaying error codes, error or failure conditions when maintenance is needed, power failure, ankle relaxer out of position, and safety condition violations.

The control panel also contains preset buttons A (496) and B (498). Pressing either button while the table is in an upright position will cause it to tilt downward toward a horizontal position and elevate to preselected height. If the table is horizontal, pressing either button A or button B (496 and 498) will cause the table change height without tilting if not already at that height. Switches A and B (496 and 498) are selectively programmed by placing table at desired height by pressing the up (484U) or down (484D) arrow buttons. Then preset button A or B (496 or 498) is held for over five seconds until the table provides an audible signal indicating that programmed selection has been stored.

The apparatus 100 is provided with a foot switch 500 for easy operation by a practitioner to return the table 102 to the 70° upstanding position (FIG. 1). Pressing the foot switch 500 during an automatic table movement operation causes the operation to stop immediately. In addition, the apparatus has a cover 502 over the base section which operates safety shut-off switches 504 in a manner similar to that shown and described in U.S. Pat. No. 4,724,554, incorporated herein by reference. The apparatus 100 also includes tilt position sensors 506 and elevation position sensors 508 of the bar code reading type providing tilt and elevation position information to the main controller 476.

Figure 48A:
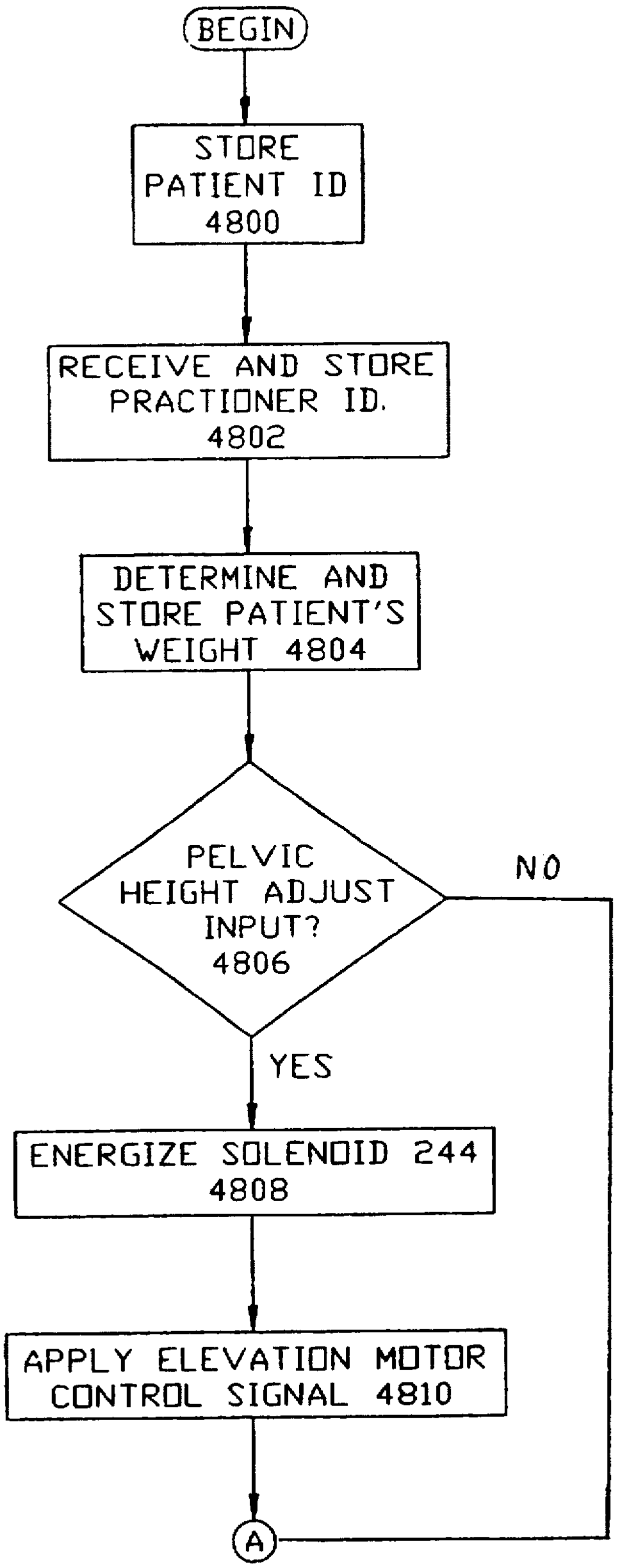
FIGS. 48A, 48B and 49C together provide a chart illustrating a learning process for a new patient.
Figure 48B:
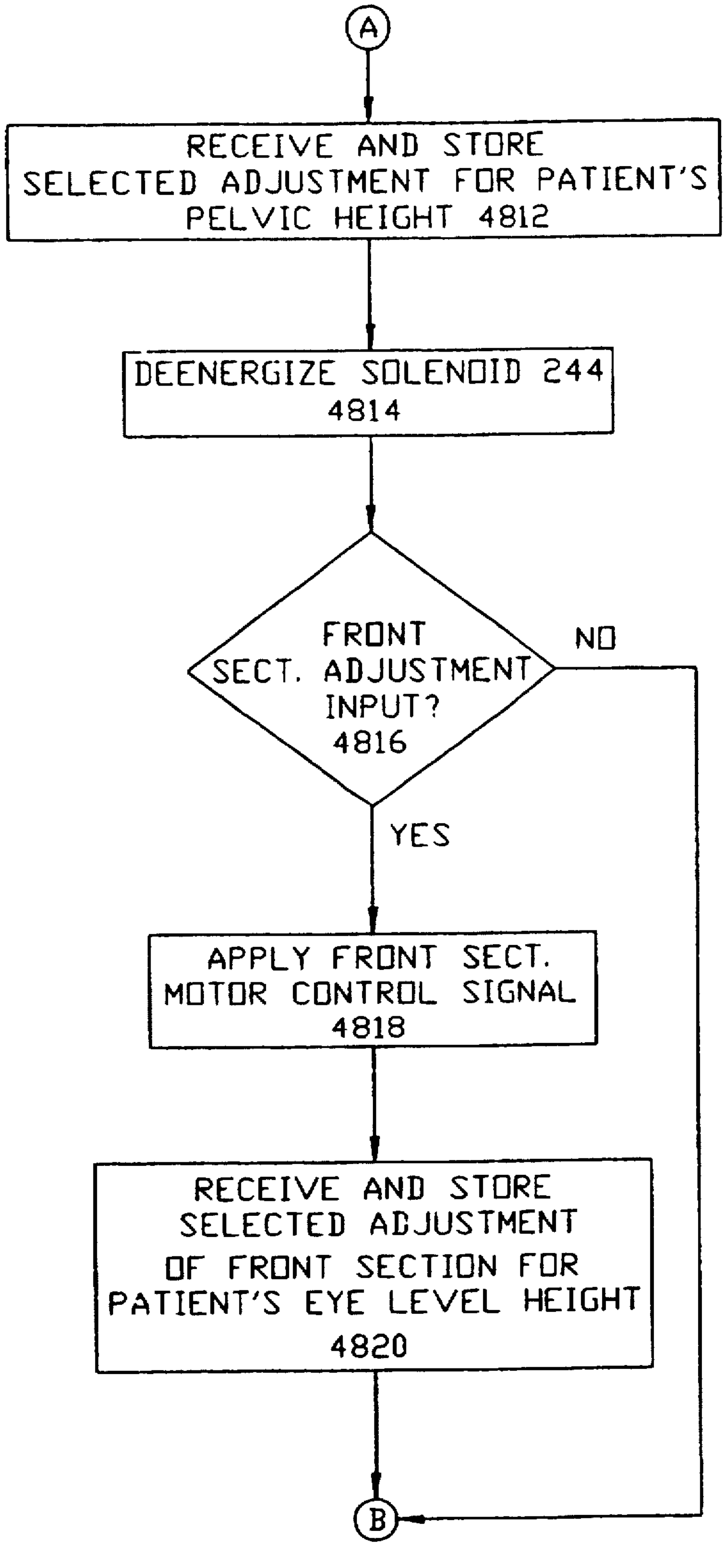
Figure 48C:
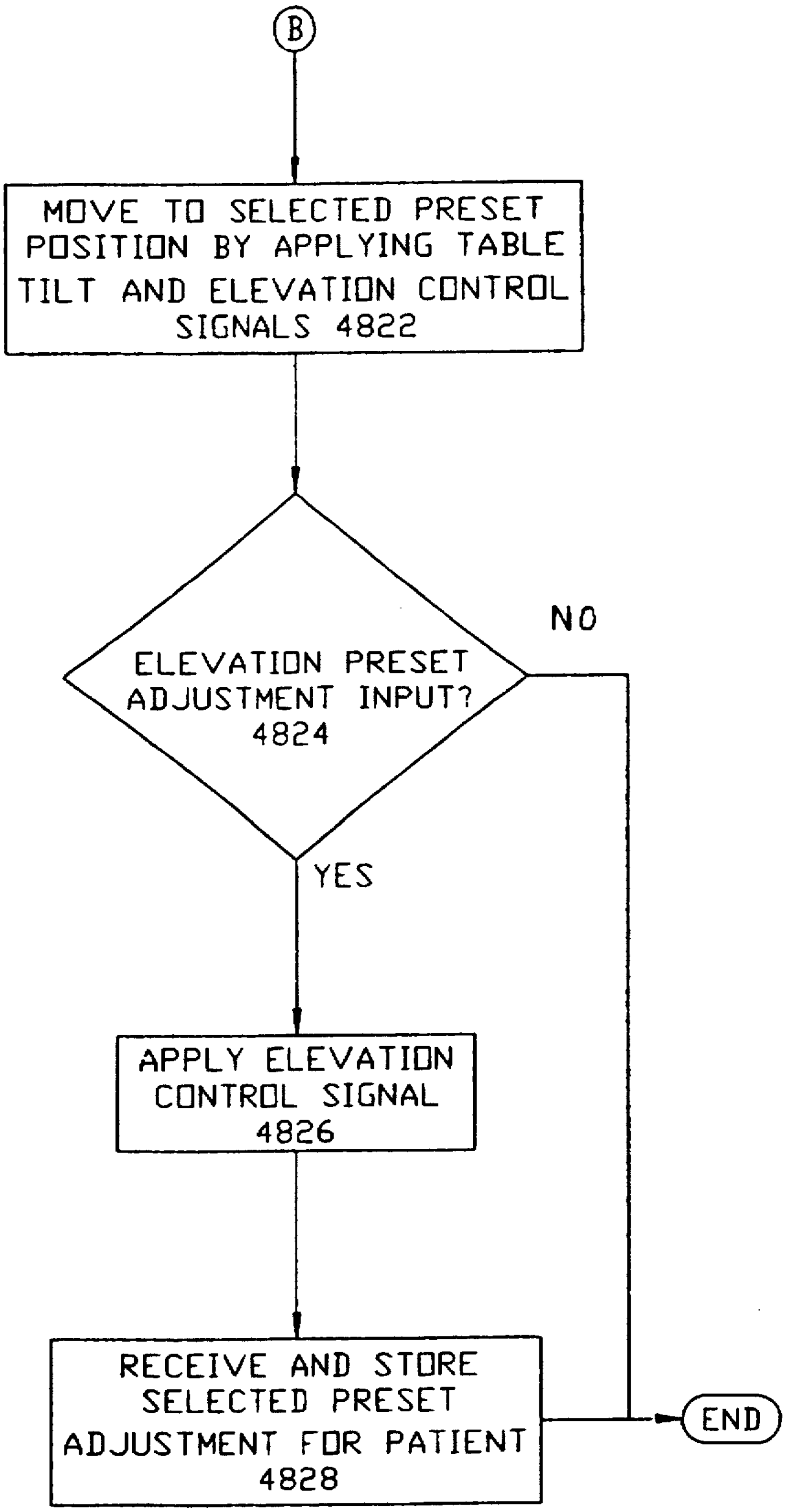

Referring now to FIGS. 48A–48C, there are shown flow charts that together illustrate sequential operations performed by the main controller or microprocessor 474 during a learning process for a new patient. Referring initially to FIG. 48A, first a patient identification received for the particular new patient is stored at a block 4800. Then the particular practitioner identification is received and stored at a block 4802. Next the patient's weight is determined and stored as indicated at a block 4804. Then the practitioner selectively operates one of the switches 484U or 484D for adjusting the table 102 to the new patient's pelvic height that is identified as indicated at a decision block 4806. Solenoid 244 is energized as indicated at a block 4808 to permit adjustment of apparatus 100 for the patient's pelvic height. As indicated at a block 4810, microprocessor 476 applies an elevation motor control signal to motor controller 464 for operatively controlling the table elevation motor 160. The height of table 102 is appropriately adjusted for the new patient's pelvic height corresponding to the practitioner's selective operations of switches 484U or 484D.

Referring to FIG. 48B following entry point A, the selected adjustment indicated by the practitioner for the patient's pelvic height is received and stored in memory 477 as indicated at a block 4812. Then solenoid 244 is deenergized as indicated at a block 4814. Then the practitioner selectively operates one of the switches 490 or 492 for adjusting the front section for the new patient's eye level height that is identified as indicated at a decision block 4816. As indicated at a clock 4818, microprocessor 476 applies a front section motor control signal to motor controller 470 for operatively controlling the front section motor 314. The front section is appropriately adjusted for the new patient's eye level height corresponding to the practitioner's selective operations of switches 490 and 492. The front section adjustment is received and stored in memory 477 as indicated at a block 4820.

Referring to FIG. 48C following entry point B, then the table can be moved to a first preset position as indicated at block 4822 by applying predetermined table tilt and elevation motor control signals to the motor controller 464. When selected by the practitioner, an elevation adjustment input is identified at a decision block 4824. As indicated at a block 4826, an elevation motor control signal is applied to the motor controller 464 corresponding to the user selective operations of switches 484U and 484D. Then the selected preset adjustment for the new patient is received and stored as indicated at a block 4828. This completes the sequential operations for the new patient learning process.

Figure 49A:
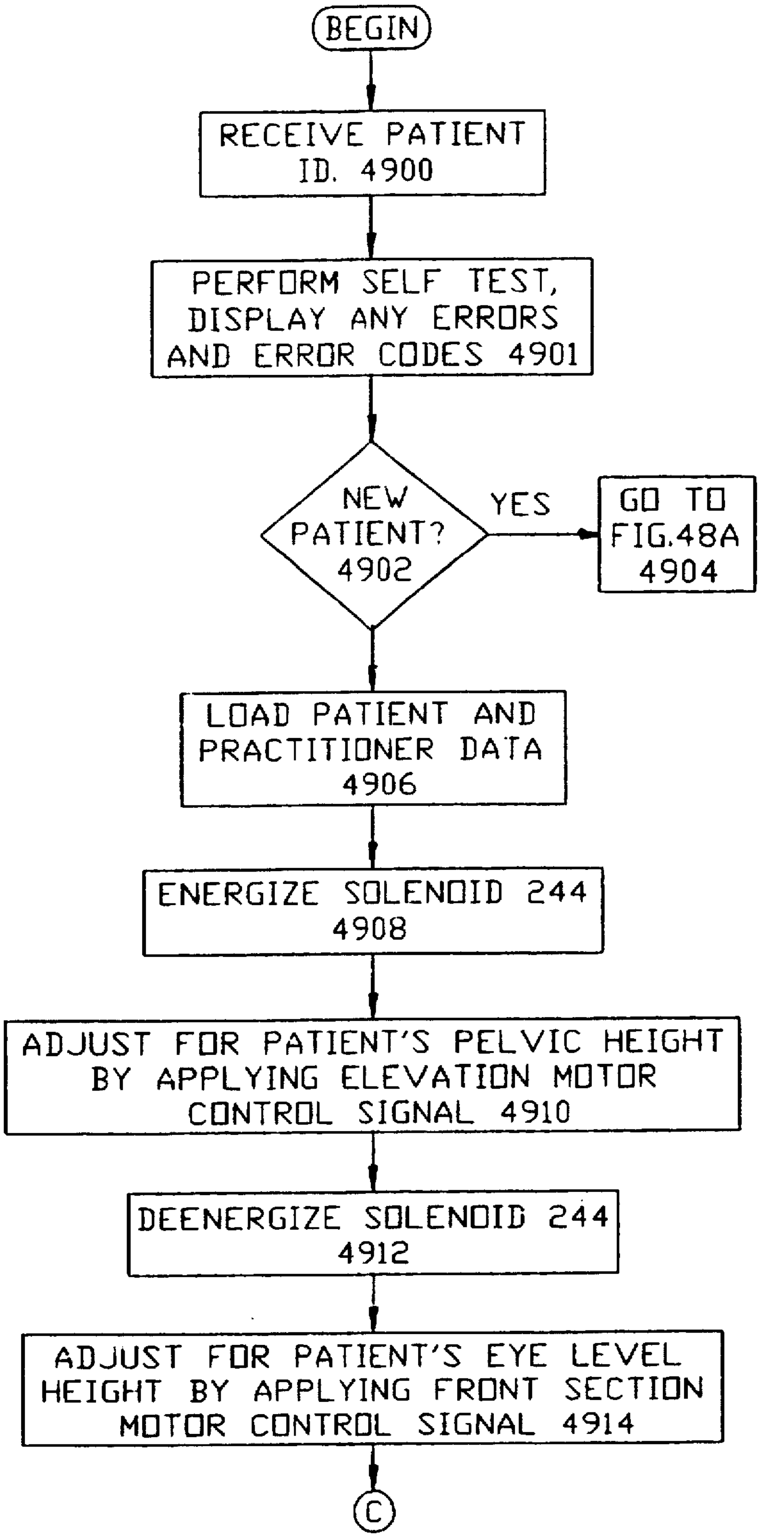
Figure 49B:
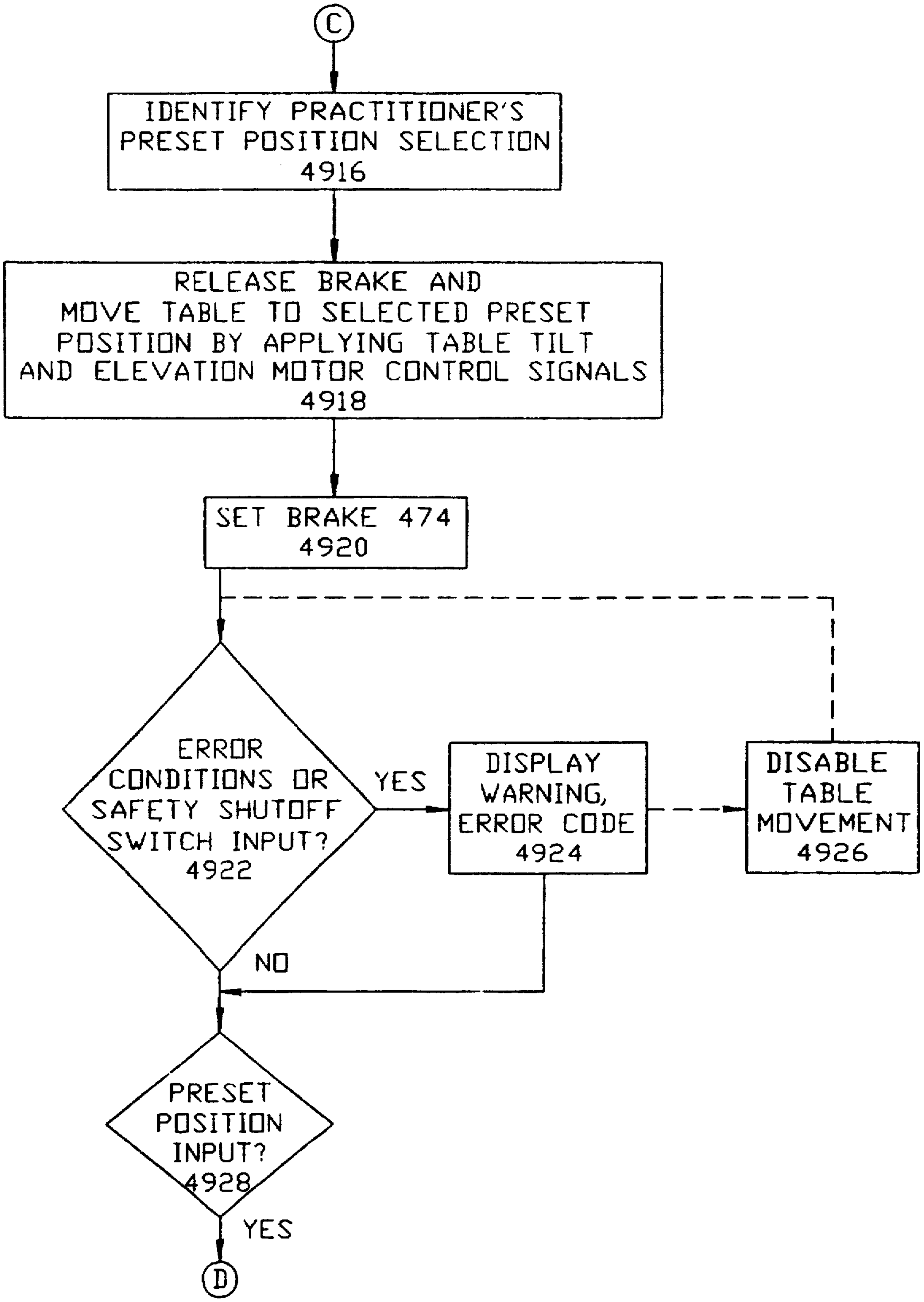
Figure 49C:
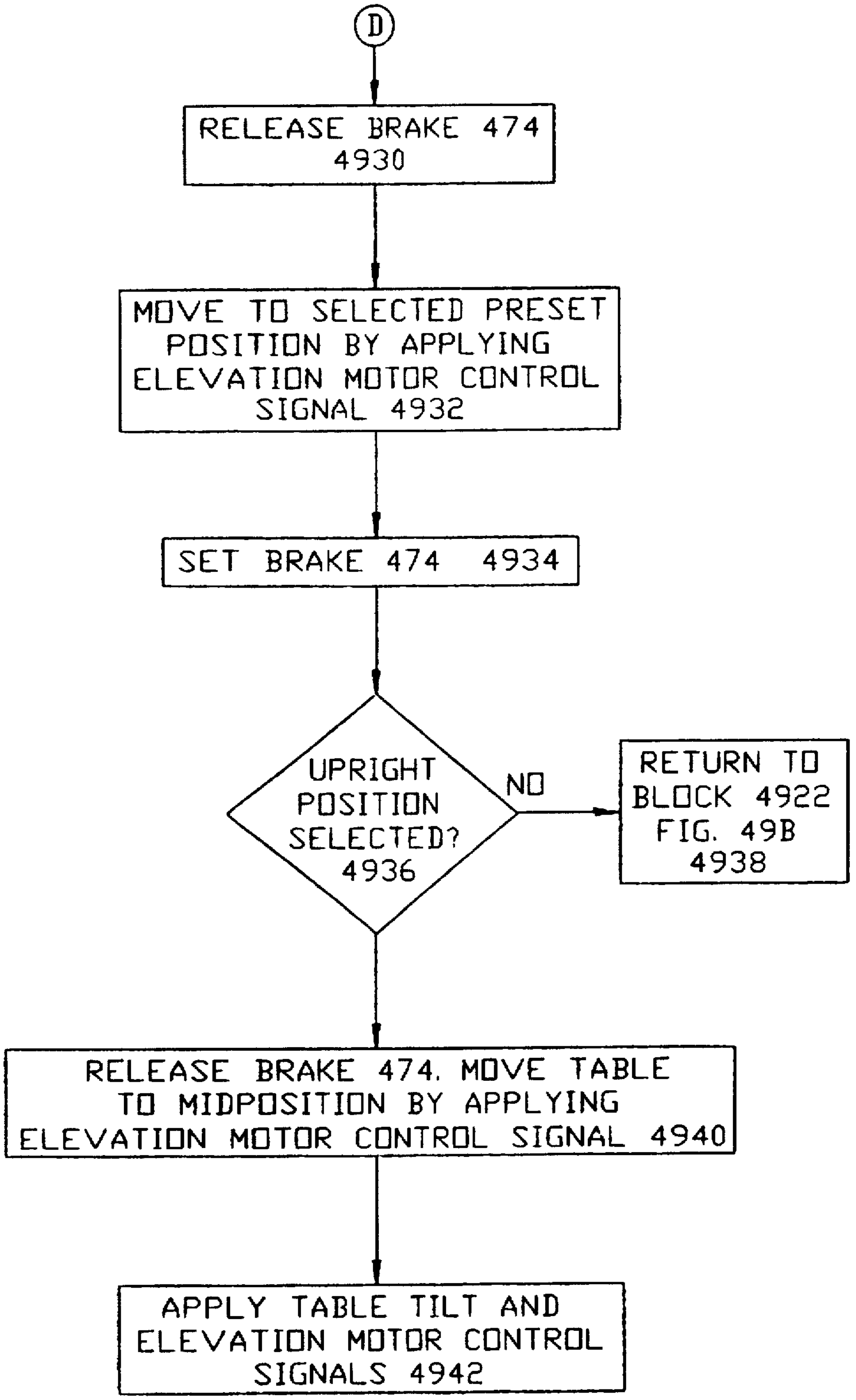

Referring now to FIGS. 49A, 49B and 49C, there are shown flow charts that together illustrate sequential operations performed by the main controller or microprocessor 476 during an operations process for the patient treatment apparatus. Initially microprocessor 476 receives a patient identification via the data entry device 479 as indicated at a block 4900 in FIG. 49A. A self-test is performed by microprocessor 476 and any identified error conditions are displayed on the LED display 481 as indicated at a block 4901. Then it is determined whether the patient is a new patient as indicated at a decision block 4902. When a new patient is identified at decision block 4902, then the sequential steps continue with the patient learning process starting with FIG. 48A as indicated at a block 4904. Otherwise, when the patient is not a new patient, then the patient and practitioner data is loaded as indicated at a block 4906. As indicated at a block 4908, solenoid 244 is energized to permit adjustment for the patient's pelvic height. Adjustment for the patient's pelvic height is provided by applying a elevation motor control signal to the motor controller 464 for operatively controlling the elevation motor 160 as indicated at a block 4910. Then solenoid 244 is deenergized as indicated at a block 4912. Adjustment for the patient's eye level height is provided by applying a front section motor control signal to the motor controller 470 for operatively controlling the front section motor 314 as indicated at a block 4914.

Referring to FIG. 49B following entry point C, then the practitioner's selection of a preset position is identified as indicated at a decision block 4916. Then the table is moved to the selected preset position as indicated at block 4918 by applying predetermined table tilt and elevation motor control signals to the motor controller 464. Then the brake is set as indicated at a block 4920. Interrupts for predetermined error conditions and predefined safety shutoff switches are identified as indicated at a decision block 4922. When any predetermined error conditions or predefined safety shutoff switches are identified, then an appropriate warning or error message is displayed on LED display 481 as indicated at a block 4924. Then as indicated at a block 4926 disabling of table movement optionally is provided depending on the particular predetermined error conditions or predefined safety shutoff switch operation that is identified at block 4922. After table movement is disabled at block 4926, then the sequential operations return to decision block 4922 until the identified condition is corrected. Otherwise, after the warning is displayed, then a practitioner's selection of a change in the table elevation or preset position is identified as indicated at a decision block 4928.

Referring to FIG. 49C following entry point D, after a change in the table elevation or preset position is identified, then the brake 474 is released as indicated at a block 4930. The table elevation or preset position is changed by applying a table elevation motor control signal to the motor controller 464 as indicated at a block 4932. Then the brake is set as indicated at a block 4934. When the treatment is completed, the practitioner's input to move the table to the upright position for patient to dismount is identified at a decision block 4936. Otherwise monitoring for error condition is continued at block 4922 in FIG. 49B as indicated at a block 4938. When the treatment is completed and the practitioner's input is identified at decision block 4936, then the table 102 is moved to the midposition by applying an elevation motor control signal to the motor controller 464 as indicated at a block 4940. Then the table tilt and elevation motor control signals are applied to the motor controller 464 as indicated at a block 4942 to move the table 102 to the dismount position.

Figure 50A:
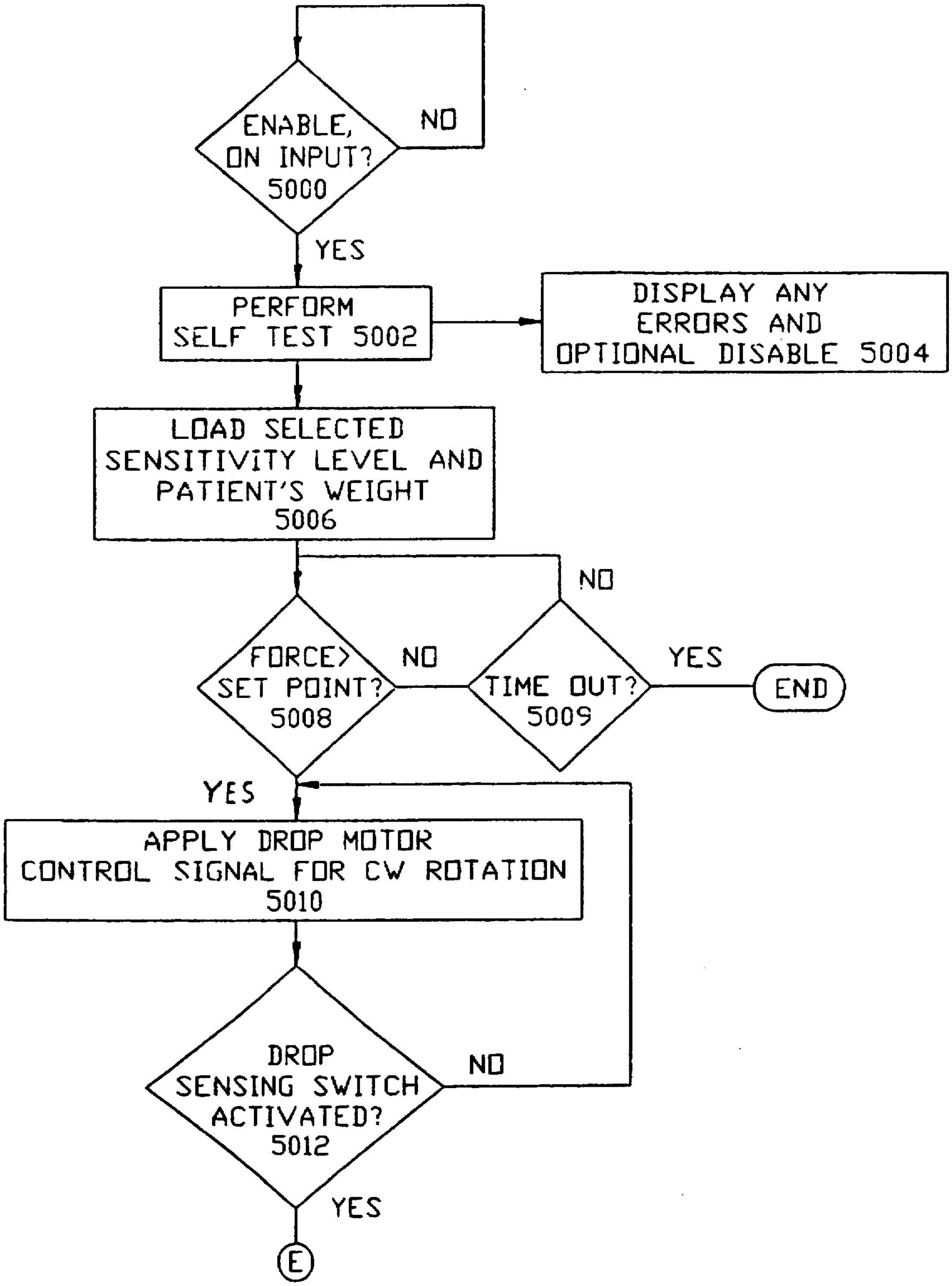
FIGS. 50A and 50B together provide a flow chart illustrating the sequential steps of a drop operation.
Figure 50B:
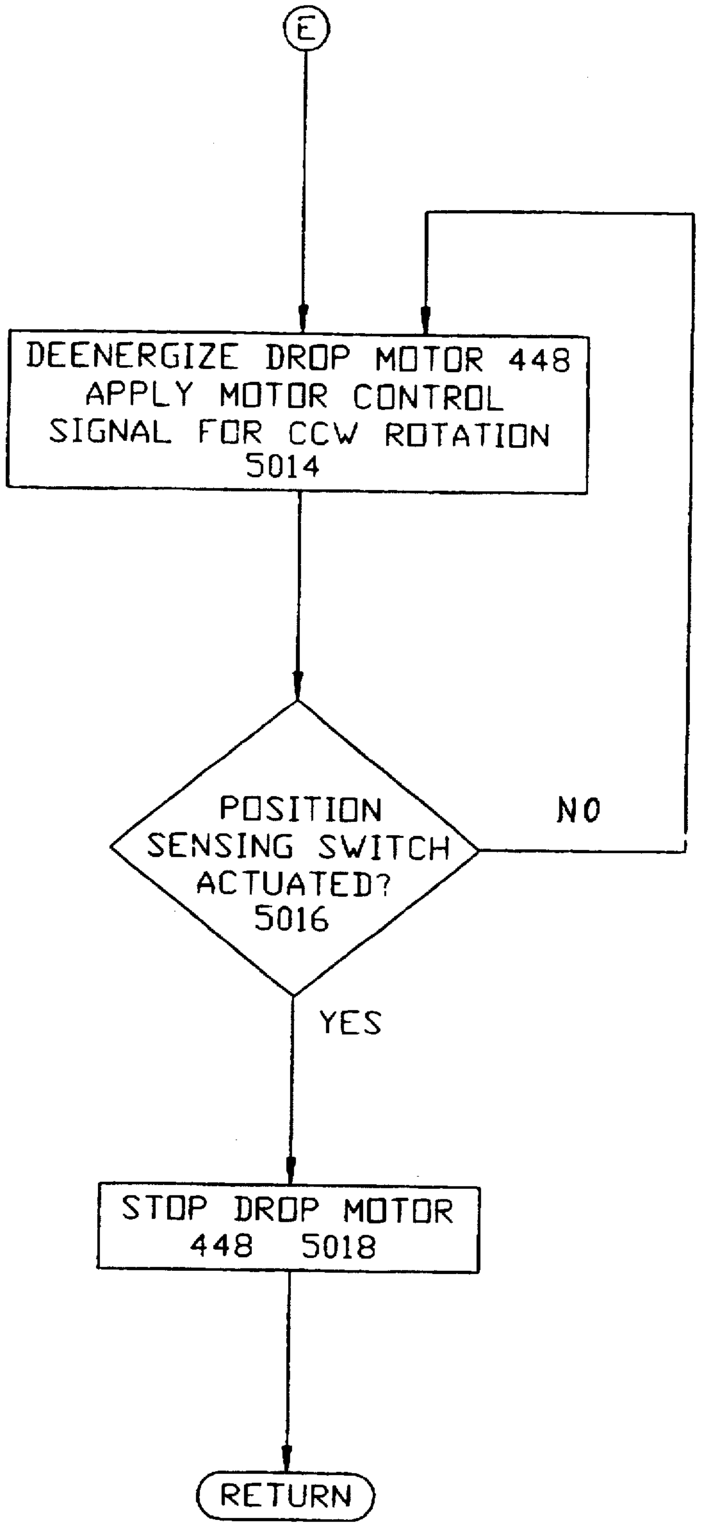

Referring now to FIGS. 50A and 50B, there are shown flow charts together illustrating sequential steps performed by the drop microprocessor 427 (FIG. 28) for a drop operation. A drop enable, power ON input selection by the practitioner is identified as indicated at a block 5000 to begin the drop operation. Microprocessor 427 performs a self-test sequence to identify any error condition related to the drop mechanism as indicated at a block 5002. Then microprocessor 427 loads the selected sensitivity level and the patient's weight as indicated at a block 5006. An applied force detected by the force transducer 426 is compared with the predefined set point determined by the patient's weight and the selected sensitivity level as indicated at a decision block 5008. A timeout predetermined time period, such as 90 seconds is identified and microprocessor 427 turns off power to the drop mechanism 390 as indicated at a decision block 5009. When the detected force exceeds the set point, then microprocessor 427 applies a drop motor control signal for clockwise rotation of shaft 450 as indicated at a block 5010. Then when the drop sensing switch 456 is actuated as indicated at a decision block 5012, the sequential operations continue with FIG. 50B.

Referring to FIG. 50B following entry point E, microprocessor 427 deenergizes the drop motor 448 and then applies a motor control signal for counterclockwise (CCW) of the shaft 450 as indicated at a block 5014. Then when the position sensing switch 458 is actuated as indicated at a decision block 5016, then microprocessor 427 deenergizes the drop motor 448 completing a drop sequence. Then the sequential operations return to block 5008 in FIG. 50A to begin a next drop sequence.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Apparatus for supporting a patient for controlled dropping movement from a first level toward a second level, said apparatus including:

power driven lift means for elevating at least a portion of the patient to said first level;

latch means for retaining said lift means at said first level; and release means for actuating said latch means to initiate a drop from said first level toward said second level in response to the exertion of a predetermined downward force on the patient; said release means includes adjustable control means for selecting the amount of said predetermined downward force for activating said release means to initiate the drop.

2. The apparatus of claim 1, including:

means for measuring the weight of the patient at said first level.

3. The apparatus of claim 1, including:

automatic means for activating said power driven lift means to return to said first level from said second level after a drop has been initiated and completed.

4. The apparatus of claim 3, wherein:

said automatic means includes means for repetitively returning said power driven lift means from said second level to said first level after successive drops.

5. The apparatus of claim 1, including:

user operated means for selecting said predetermined downward forces.

6. The apparatus of claim 1, wherein:

said release means includes an electric motor.

7. The apparatus of claim 1, including:

support means for said patient permitting limited movement during the drop in a sloped direction angularly away from a vertical downward direction.

8. The apparatus of claim 7, wherein:

said support means includes limit means for permitting free limited movement during a drop in said sloped angular direction as determined by the direction of force exerted on the patient to initiate said drop.

9. The apparatus of claim 8, wherein:

said support means includes stop means for limiting the amount of angular deviation between said sloped angular drop direction and the vertical downward direction during a drop.

10. The apparatus of claim 9, wherein:

said angular deviation limit is defined within a conical envelope having an upper apex at the vertical direction from where a drop is initiated.

11. The apparatus of claim 7, including:

control means selectively operable to permit only a vertically downward direction of drop in a first condition and to permit a drop sloping in an angular path away from vertical in a second condition.

12. The apparatus of claim 11, wherein:

said control means includes first stop means for limiting a drop sloping in an angular position away from vertical to a single first vertical plane.

13. The apparatus of claim 12, wherein:

said control means includes second stop means for limiting a drop sloping in an angular position away from vertical to a single second vertical plane angularly disposed to said first vertical plane.

14. The apparatus of claim 12, wherein:

said first vertical plane is generally aligned with a spinal axis of a supported patient.

15. The apparatus of claim 13, wherein:

said second vertical plane is generally aligned transversely to the spinal axis of a supported patient.

16. The apparatus of claim 12, wherein:

said first vertical plane is generally aligned transversely to the spinal axis of a supported patient.

17. Drop apparatus for supporting a patient for selectively controlled dropping movement from a first level toward a second level, including:

lift means for raising a portion of the patient from said second level to said first level in position for a drop;

latch means for securing said lift means at said first level releasable by a predetermined downward force applied on said patient;

guide means for controlling a path of the drop from said first level toward said second level; and automatic means for actuating said lift means to elevate to said first level from said second level after a drop is completed.

18. The apparatus of claim 17, wherein:

said automatic means includes means for repetitively repeating return of said lift means to said first level from said second level after successive drops.

19. The apparatus of claim 17, including:

user operated means for selecting said predetermined downward force.

20. The apparatus of claim 17, wherein:

said latch means includes an electric motor.

21. The apparatus of claim 17, including:

means for measuring the weight of the patient at said first level.

22. The apparatus of claim 17, wherein:

said guide means directs said drop along a substantially straight drop path.

23. The apparatus of claim 17, wherein said guide means permits said drop to spiral downwardly along a curved path.

24. The apparatus of claim 23, wherein:

said curved path comprises a downward spiral.

25. The apparatus of claim 17, wherein:

said guide means confines said drop path to lie in a single vertical plane.

26. The apparatus of claim 25, wherein:

said single vertical plane is aligned with a spinal axis of a supported patient.

27. The apparatus of claim 25, wherein:

said single vertical plane is aligned transversely across a spinal axis of a supported patient.

* * * * *